(12) United States Patent
Cozean

(10) Patent No.: US 8,298,320 B2
(45) Date of Patent: *Oct. 30, 2012

(54) SYSTEMS FOR REMOVING DIMETHYL SULFOXIDE (DMSO) OR RELATED COMPOUNDS, OR ODORS ASSOCIATED WITH SAME

(75) Inventor: Colette Cozean, Lake Forest, CA (US)

(73) Assignee: Abela Pharmaceuticals, Inc., Lake Forest, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,098

(22) Filed: May 2, 2011

(65) Prior Publication Data

US 2011/0203584 A1    Aug. 25, 2011

Related U.S. Application Data

(63) Continuation of application No. 12/066,485, filed as application No. PCT/US2006/035321 on Sep. 11, 2006, now Pat. No. 7,955,418.

(60) Provisional application No. 60/716,271, filed on Sep. 12, 2005, provisional application No. 60/716,336, filed on Sep. 12, 2005, provisional application No. 60/716,278, filed on Sep. 12, 2005, provisional application No. 60/716,369, filed on Sep. 12, 2005.

(51) Int. Cl.
*A61L 9/014* (2006.01)
*A62B 7/10* (2006.01)

(52) U.S. Cl. .................. 95/135; 95/141; 128/205.27

(58) Field of Classification Search .............. 95/135, 95/137, 141; 128/206.12, 203.29, 205.27, 128/205.25, 206.21, 205.26; 423/244.01
See application file for complete search history.

(56) References Cited

U.S. PATENT DOCUMENTS

| | | | |
|---|---|---|---|
| 3,334,012 A | 8/1967 | Herschler |
| 3,361,555 A | 1/1968 | Herschler |
| 3,393,080 A | 7/1968 | Erdi et al. |
| 3,419,619 A | 12/1968 | Soder et al. |
| 3,482,572 A | 12/1969 | Grosclaude et al. |
| 3,527,863 A | 9/1970 | Weichselbaum |
| 3,549,770 A | 12/1970 | Herschler et al. |
| 3,549,771 A | 12/1970 | Herschler |
| 3,551,554 A | 12/1970 | Herschler |
| 3,558,434 A | 1/1971 | Herschler |
| 3,573,214 A | 3/1971 | Kollonitsch |
| 3,592,936 A | 7/1971 | Marcus et al. |
| 3,654,165 A | 4/1972 | Bryant et al. |

(Continued)

FOREIGN PATENT DOCUMENTS

CA    2617934    2/2007

(Continued)

OTHER PUBLICATIONS

Aleksevich Ial, Piletskaia IG, Nikonorova VP. *Increase in the sensitivity of the microflora of pathological gingival pockets to streptomycin under the influence of dimexide and trypsin*. Mikrobiol Zh. Nov.-Dec. 1973; 35(6):766-9.

(Continued)

*Primary Examiner* — Frank Lawrence, Jr.
(74) *Attorney, Agent, or Firm* — Knobbe Martens Olson & Bear, LLP

(57) ABSTRACT

Preferred embodiments of the invention relate to systems for removing dimethyl sulfoxide (DMSO) or related compounds, or odors associated with same. The systems include adsorbents, odor adsorbing fabrics, masks, clean air members and clean air supply assemblies.

18 Claims, 5 Drawing Sheets

U.S. PATENT DOCUMENTS

| | | | |
|---|---|---|---|
| 3,675,654 A | 7/1972 | Baker et al. |
| 3,690,808 A | 9/1972 | St. Pierre |
| 3,711,606 A | 1/1973 | Herschler |
| 3,740,420 A | 6/1973 | Herschler et al. |
| 3,773,838 A | 11/1973 | Andruski et al. |
| 3,790,682 A | 2/1974 | Herschler et al. |
| 3,823,676 A | 7/1974 | Cook et al. |
| 3,852,408 A | 12/1974 | Ewan et al. |
| 3,861,894 A | 1/1975 | Marsh |
| 3,881,003 A | 4/1975 | Rehm |
| 3,948,617 A | 4/1976 | Withorn |
| 3,972,962 A | 8/1976 | Williams et al. |
| 3,976,747 A | 8/1976 | Shale et al. |
| 3,988,129 A | 10/1976 | Fornoff et al. |
| 3,996,295 A | 12/1976 | Goeb |
| 4,015,025 A | 3/1977 | Szczesniak |
| 4,112,946 A | 9/1978 | Herschler |
| 4,125,589 A | 11/1978 | deVries |
| 4,129,122 A | 12/1978 | Dout et al. |
| 4,169,550 A | 10/1979 | Williams |
| 4,177,267 A | 12/1979 | Herschler |
| 4,194,628 A | 3/1980 | Campos |
| 4,202,676 A | 5/1980 | Pelosi, Jr. et al. |
| 4,212,392 A | 7/1980 | McKenzie |
| 4,225,381 A | 9/1980 | Ishikawa et al. |
| 4,252,054 A | 2/1981 | Bakels |
| 4,256,728 A | 3/1981 | Nishino et al. |
| 4,277,450 A | 7/1981 | Dilworth |
| 4,296,104 A | 10/1981 | Herschler |
| 4,296,130 A | 10/1981 | Herschler |
| 4,307,067 A | 12/1981 | Tagawa et al. |
| 4,309,393 A | 1/1982 | Nguyen |
| 4,316,795 A | 2/1982 | Mooi |
| 4,333,922 A | 6/1982 | Herschler |
| 4,335,148 A | 6/1982 | Vidal et al. |
| 4,341,675 A | 7/1982 | Nakamura |
| 4,350,245 A | 9/1982 | Elstner |
| 4,357,288 A | 11/1982 | Oas et al. |
| 4,369,190 A | 1/1983 | Schulte |
| 4,372,915 A | 2/1983 | Neti et al. |
| 4,413,109 A | 11/1983 | Haas |
| 4,424,330 A | 1/1984 | Raviola |
| 4,469,702 A | 9/1984 | Schulte |
| 4,477,469 A | 10/1984 | Herschler |
| 4,491,563 A | 1/1985 | Reusser et al. |
| 4,493,930 A | 1/1985 | Klayman et al. |
| 4,497,824 A | 2/1985 | Schulte |
| 4,505,708 A | 3/1985 | Gajewski et al. |
| 4,510,292 A | 4/1985 | Chiba et al. |
| 4,512,245 A | 4/1985 | Goldman |
| 4,514,421 A | 4/1985 | Herschler |
| 4,545,414 A | 10/1985 | Baum |
| 4,550,010 A | 10/1985 | Chelu |
| 4,559,329 A | 12/1985 | Herschler |
| 4,568,547 A | 2/1986 | Herschler |
| 4,575,515 A | 3/1986 | Sandborn |
| 4,591,497 A | 5/1986 | Naito et al. |
| 4,595,102 A | 6/1986 | Cianci et al. |
| 4,600,002 A | 7/1986 | Maryyanek et al. |
| 4,616,039 A | 10/1986 | Herschler |
| 4,616,064 A | 10/1986 | Zukosky et al. |
| 4,622,221 A | 11/1986 | Schleppnik |
| 4,626,530 A | 12/1986 | Schulte |
| 4,634,588 A | 1/1987 | Moroe |
| 4,642,177 A | 2/1987 | Mester et al. |
| 4,652,557 A | 3/1987 | Sandborn |
| 4,655,148 A | 4/1987 | Winship |
| 4,656,094 A | 4/1987 | Kojima et al. |
| 4,686,204 A | 8/1987 | Mester et al. |
| 4,710,353 A | 12/1987 | Tanaka et al. |
| 4,719,105 A | 1/1988 | Schleppnik |
| 4,721,813 A | 1/1988 | Mark et al. |
| 4,725,290 A | 2/1988 | Ohlmeyer et al. |
| 4,728,712 A | 3/1988 | Singh et al. |
| 4,729,835 A | 3/1988 | McNeillie et al. |
| 4,737,173 A | 4/1988 | Kudirka et al. |
| 4,747,845 A | 5/1988 | Korol |
| 4,751,241 A | 6/1988 | Motoyama et al. |
| 4,778,697 A | 10/1988 | Genske et al. |
| 4,784,909 A | 11/1988 | Emi et al. |
| 4,796,790 A | 1/1989 | Hamilton |
| 4,797,274 A | 1/1989 | Miki et al. |
| 4,803,047 A | 2/1989 | Pluim, Jr. |
| 4,830,718 A | 5/1989 | Stauffer |
| 4,834,721 A | 5/1989 | Onohara et al. |
| 4,850,268 A | 7/1989 | Saito et al. |
| 4,863,687 A | 9/1989 | Stevens et al. |
| 4,863,748 A | 9/1989 | Herschler |
| 4,887,751 A | 12/1989 | Lehman |
| 4,902,489 A | 2/1990 | Watanabe |
| 4,902,558 A | 2/1990 | Henriksen |
| 4,904,520 A | 2/1990 | Dumas et al. |
| 4,910,803 A | 3/1990 | Cukier |
| 4,911,691 A | 3/1990 | Aniuk et al. |
| 4,914,135 A | 4/1990 | Herschler |
| 4,916,767 A | 4/1990 | Uetake et al. |
| 4,919,925 A | 4/1990 | Ueda et al. |
| 4,931,276 A | 6/1990 | Franco et al. |
| 4,937,115 A | 6/1990 | Leatherman |
| 4,940,405 A | 7/1990 | Kelly |
| 4,940,658 A | 7/1990 | Allen et al. |
| 4,941,991 A | 7/1990 | Rajamannan |
| 4,946,720 A | 8/1990 | Oishi et al. |
| 4,948,643 A | 8/1990 | Mueller |
| 4,948,787 A | 8/1990 | Chen et al. |
| 4,956,183 A | 9/1990 | Miki et al. |
| 4,973,605 A | 11/1990 | Herschler |
| 4,978,687 A | 12/1990 | Pascuchi |
| 4,980,045 A | 12/1990 | Krishna et al. |
| 4,988,505 A | 1/1991 | Watanabe et al. |
| 4,990,311 A | 2/1991 | Hirai et al. |
| 4,994,245 A | 2/1991 | Murray et al. |
| 5,001,794 A | 3/1991 | Uetake et al. |
| 5,006,510 A | 4/1991 | Ellis |
| 5,007,999 A | 4/1991 | Chin |
| 5,032,613 A | 7/1991 | Watson |
| 5,041,273 A | 8/1991 | Rock |
| 5,049,159 A | 9/1991 | Yamaji et al. |
| 5,049,163 A | 9/1991 | Huang et al. |
| 5,055,279 A | 10/1991 | Hirt et al. |
| 5,059,477 A | 10/1991 | Henriksen |
| 5,070,597 A | 12/1991 | Holt et al. |
| 5,071,622 A | 12/1991 | Dunson, Jr. |
| 5,071,686 A | 12/1991 | Genske et al. |
| 5,071,878 A | 12/1991 | Herschler |
| 5,083,558 A | 1/1992 | Thomas et al. |
| 5,086,804 A | 2/1992 | Ngai |
| 5,087,673 A | 2/1992 | Watanabe et al. |
| 5,091,180 A | 2/1992 | Walker et al. |
| 5,117,821 A | 6/1992 | White |
| 5,133,788 A | 7/1992 | Backus |
| 5,135,904 A | 8/1992 | Kamiya et al. |
| 5,139,831 A | 8/1992 | Mueller |
| 5,143,831 A | 9/1992 | Wong et al. |
| 5,145,657 A | 9/1992 | Kobayashi et al. |
| 5,149,576 A | 9/1992 | Potts et al. |
| 5,152,814 A | 10/1992 | Nelson |
| 5,160,707 A | 11/1992 | Murray et al. |
| 5,169,217 A | 12/1992 | Orchard et al. |
| 5,183,656 A | 2/1993 | Uesaka et al. |
| 5,190,640 A | 3/1993 | Roof et al. |
| 5,192,272 A | 3/1993 | Faure |
| 5,192,342 A | 3/1993 | Baron et al. |
| 5,192,498 A | 3/1993 | Chen et al. |
| 5,199,263 A | 4/1993 | Green et al. |
| 5,207,303 A | 5/1993 | Oswalt et al. |
| 5,213,680 A | 5/1993 | Kremer et al. |
| 5,218,036 A | 6/1993 | Kagawa et al. |
| 5,218,147 A | 6/1993 | Shaw |
| 5,240,478 A | 8/1993 | Messina |
| 5,260,090 A | 11/1993 | Isao |
| 5,269,294 A | 12/1993 | Rogozinski |
| 5,290,331 A | 3/1994 | Miles et al. |
| 5,336,431 A | 8/1994 | Richards et al. |
| 5,344,529 A | 9/1994 | Stauffer |
| 5,356,709 A | 10/1994 | Woo et al. |
| 5,358,443 A | 10/1994 | Mitchell et al. |

| | | | | | | |
|---|---|---|---|---|---|---|
| 5,409,769 | A | 4/1995 | Fukumoto et al. | D431,353 S | 10/2000 | Mellin |
| 5,415,180 | A | 5/1995 | Horan | D431,902 S | 10/2000 | Mellin |
| 5,419,812 | A | 5/1995 | Beal | 6,183,708 B1 | 2/2001 | Hei et al. |
| 5,439,454 | A | 8/1995 | Lo et al. | 6,183,758 B1 | 2/2001 | Scott |
| 5,441,729 | A | 8/1995 | Salce et al. | 6,197,288 B1 | 3/2001 | Mankoo |
| 5,458,848 | A | 10/1995 | Burgaud | 6,207,106 B1 | 3/2001 | Kurokawa et al. |
| 5,458,861 | A | 10/1995 | Buchanan et al. | 6,221,325 B1 | 4/2001 | Brown et al. |
| 5,460,625 | A | 10/1995 | Johnson | 6,228,960 B1 | 5/2001 | Tanaglia |
| 5,466,757 | A | 11/1995 | Watanabe et al. | 6,238,767 B1 | 5/2001 | McCormack et al. |
| 5,480,860 | A | 1/1996 | Dillon | 6,248,733 B1 | 6/2001 | Landgrebe et al. |
| 5,486,387 | A | 1/1996 | Mueller | 6,261,655 B1 | 7/2001 | Rosenbaum et al. |
| 5,487,766 | A | 1/1996 | Vannier | 6,267,941 B1 | 7/2001 | Sata |
| 5,494,587 | A | 2/1996 | Morlec et al. | 6,277,344 B1 | 8/2001 | Hei et al. |
| 5,512,144 | A | 4/1996 | Stauffer | 6,294,161 B1 | 9/2001 | Hiramoto et al. |
| 5,516,526 | A | 5/1996 | De la Torre | 6,303,200 B1 | 10/2001 | Woo et al. |
| 5,521,268 | A | 5/1996 | Ghyzel et al. | 6,312,713 B1 | 11/2001 | Korol et al. |
| 5,531,987 | A | 7/1996 | Bauer et al. | 6,318,075 B1 | 11/2001 | Gunther et al. |
| 5,538,545 | A | 7/1996 | Dauber et al. | 6,348,177 B1 | 2/2002 | Bartley et al. |
| 5,562,127 | A | 10/1996 | Fanselow et al. | 6,349,826 B1 | 2/2002 | Kapik et al. |
| 5,569,679 | A | 10/1996 | Jacob | 6,365,099 B1 | 4/2002 | Castrantas et al. |
| 5,578,540 | A | 11/1996 | Banzi et al. | 6,403,642 B1 | 6/2002 | Berg |
| 5,584,986 | A | 12/1996 | Bartholic | 6,403,739 B1 | 6/2002 | Tanaglia et al. |
| 5,603,696 | A | 2/1997 | Williams et al. | 6,406,767 B1 | 6/2002 | Mueller |
| 5,605,635 | A | 2/1997 | David | 6,412,639 B1 | 7/2002 | Hickey |
| 5,616,408 | A | 4/1997 | Oleszczuk et al. | 6,414,194 B1 | 7/2002 | Bloom, Jr. et al. |
| 5,620,760 | A | 4/1997 | Galimberti et al. | 6,416,772 B1 | 7/2002 | Van Engelen et al. |
| 5,624,649 | A | 4/1997 | Gal | 6,418,932 B2 | 7/2002 | Paschal, Jr. et al. |
| 5,650,329 | A | 7/1997 | Warner | 6,426,112 B1 | 7/2002 | Boatright |
| 5,654,061 | A | 8/1997 | Visioli | 6,426,370 B1 | 7/2002 | Hofschneider |
| 5,658,801 | A | 8/1997 | Poissant et al. | 6,432,891 B1 | 8/2002 | O'Connor |
| 5,667,799 | A | 9/1997 | Caldwell et al. | 6,440,391 B1 | 8/2002 | Jacob |
| 5,703,152 | A | 12/1997 | Ohama | 6,454,097 B1 | 9/2002 | Blanco |
| 5,712,044 | A | 1/1998 | Fanselow et al. | 6,458,828 B1 | 10/2002 | Sakurai et al. |
| 5,725,893 | A | 3/1998 | Pittet et al. | 6,460,702 B2 | 10/2002 | Hammond |
| 5,753,696 | A | 5/1998 | Shealy et al. | 6,461,631 B1 | 10/2002 | Dunn et al. |
| 5,761,362 | A | 6/1998 | Yang et al. | 6,465,068 B1 | 10/2002 | Patel et al. |
| 5,779,679 | A | 7/1998 | Shaw | 6,468,259 B1 | 10/2002 | Loretti et al. |
| 5,783,269 | A | 7/1998 | Heilmann et al. | 6,475,466 B1 | 11/2002 | Ricci et al. |
| 5,789,046 | A | 8/1998 | Mueller | 6,479,150 B1 | 11/2002 | Liu et al. |
| 5,792,505 | A | 8/1998 | Fulger et al. | 6,479,488 B1 | 11/2002 | Di-Fabio et al. |
| 5,803,130 | A | 9/1998 | Robben et al. | 6,482,377 B2 | 11/2002 | Bartley et al. |
| 5,803,249 | A | 9/1998 | Harsanyi, Jr. et al. | 6,495,096 B1 | 12/2002 | Hamaguchi et al. |
| 5,843,420 | A | 12/1998 | Bauer et al. | 6,528,080 B2 | 3/2003 | Dunn et al. |
| 5,849,846 | A | 12/1998 | Chen et al. | 6,531,111 B1 | 3/2003 | Whalen, II et al. |
| 5,861,096 | A | 1/1999 | Mason et al. | 6,552,231 B2 | 4/2003 | Jones et al. |
| 5,871,562 | A | 2/1999 | Culoso | 6,562,447 B2 | 5/2003 | Wu et al. |
| 5,885,566 | A | 3/1999 | Goldberg | 6,579,444 B2 | 6/2003 | Feimer et al. |
| 5,891,508 | A | 4/1999 | Barnum | 6,579,543 B1 | 6/2003 | McClung |
| 5,919,877 | A | 7/1999 | Tanaglia | 6,599,472 B1 | 7/2003 | Hudson |
| 5,928,744 | A | 7/1999 | Heilmann et al. | 6,620,911 B1 | 9/2003 | Pettit et al. |
| 5,931,303 | A | 8/1999 | Salvadori | 6,638,605 B1 | 10/2003 | Ankuda, Jr. et al. |
| 5,935,412 | A | 8/1999 | Brainard, II | 6,639,110 B2 | 10/2003 | Fremy |
| 5,935,547 | A | 8/1999 | LeComte et al. | 6,649,193 B1 | 11/2003 | Colic |
| 5,948,398 | A | 9/1999 | Hanamoto et al. | 6,652,845 B2 | 11/2003 | Hu et al. |
| 5,958,502 | A | 9/1999 | Fulger et al. | 6,653,352 B2 | 11/2003 | Barr et al. |
| 5,967,061 | A | 10/1999 | Ashworth et al. | 6,656,723 B1 | 12/2003 | Phillips |
| 5,972,993 | A | 10/1999 | Ptchelintsev | 6,663,679 B1 | 12/2003 | Duncan |
| 5,989,497 | A | 11/1999 | Labonte, Jr. | 6,680,194 B1 | 1/2004 | Turner |
| 5,998,019 | A | 12/1999 | Rosenbaum et al. | 6,706,257 B1 | 3/2004 | McCook et al. |
| 6,007,520 | A | 12/1999 | Sudo | 6,718,914 B2 | 4/2004 | Riddles |
| 6,010,666 | A | 1/2000 | Kurokawa et al. | 6,722,295 B2 | 4/2004 | Zauderer |
| 6,012,586 | A | 1/2000 | Misra | 6,723,349 B1 | 4/2004 | Hill et al. |
| 6,015,536 | A | 1/2000 | Lokkesmoe et al. | 6,723,399 B2 | 4/2004 | Chundury et al. |
| 6,030,494 | A | 2/2000 | Hupa et al. | 6,734,263 B2 | 5/2004 | Eadara et al. |
| 6,042,640 | A | 3/2000 | Isganitis et al. | 6,737,031 B2 | 5/2004 | Beal et al. |
| 6,045,596 | A | 4/2000 | Holland, Jr. et al. | 6,737,089 B2 | 5/2004 | Wadsworth et al. |
| 6,048,733 | A | 4/2000 | Machino et al. | 6,743,523 B1 | 6/2004 | Woo et al. |
| 6,057,018 | A | 5/2000 | Schmidt | 6,743,951 B2 | 6/2004 | Fremy |
| 6,060,083 | A | 5/2000 | Dorr et al. | 6,761,169 B2 | 7/2004 | Eswarappa |
| D427,299 | S | 6/2000 | Haslebacher | 6,761,912 B2 | 7/2004 | Forusz et al. |
| 6,070,578 | A | 6/2000 | Baughman et al. | 6,764,566 B1 | 7/2004 | Griesbach, III et al. |
| 6,077,335 | A | 6/2000 | Schneider et al. | 6,783,004 B2 | 8/2004 | Rinner |
| 6,090,076 | A | 7/2000 | Lane, Jr. | RE38,597 E | 9/2004 | Lane, Jr. |
| 6,094,549 | A | 7/2000 | Hiraoka et al. | 6,796,958 B2 | 9/2004 | Chen et al. |
| 6,099,607 | A | 8/2000 | Haslebacher | 6,822,015 B2 | 11/2004 | Muraki |
| 6,106,502 | A | 8/2000 | Richmond | 6,830,794 B2 | 12/2004 | Cartledge et al. |
| 6,106,596 | A | 8/2000 | Haramoto et al. | 6,844,430 B2 | 1/2005 | Pesce et al. |
| 6,110,176 | A | 8/2000 | Shapira | 6,846,535 B2 | 1/2005 | De Groot et al. |
| 6,114,586 | A | 9/2000 | Devaux et al. | 6,858,192 B2 | 2/2005 | Graham et al. |

| | | |
|---|---|---|
| 6,872,241 B2 | 3/2005 | Soane et al. |
| 6,881,419 B2 | 4/2005 | Lovett |
| 6,884,797 B2 | 4/2005 | Hofmann |
| 6,890,373 B2 | 5/2005 | Nemoto et al. |
| 6,902,714 B2 | 6/2005 | Skaarup Jensen et al. |
| 6,908,885 B2 | 6/2005 | Bengs et al. |
| 6,927,305 B2 | 8/2005 | Choudary et al. |
| 7,057,016 B2 | 6/2006 | Cerletti |
| 7,203,974 B2 | 4/2007 | Jones et al. |
| 7,282,224 B1 | 10/2007 | Roederer et al. |
| 7,371,407 B2 | 5/2008 | Farmer |
| 7,381,521 B2 | 6/2008 | Whitaker et al. |
| 7,955,418 B2 | 6/2011 | Claussen et al. |
| 2001/0005766 A1 | 6/2001 | Fremy |
| 2001/0047038 A1 | 11/2001 | Moorman et al. |
| 2002/0015762 A1 | 2/2002 | Quinlan |
| 2002/0025983 A1 | 2/2002 | Horrobin |
| 2002/0032131 A1 | 3/2002 | O'Connor |
| 2002/0043501 A1 | 4/2002 | Irvine |
| 2002/0090398 A1 | 7/2002 | Dunn et al. |
| 2002/0110549 A1 | 8/2002 | Till |
| 2002/0115729 A1 | 8/2002 | Yang |
| 2002/0131933 A1 | 9/2002 | Delmotte |
| 2002/0133100 A1 | 9/2002 | Paschal, Jr. et al. |
| 2002/0151753 A1 | 10/2002 | Fremy |
| 2002/0156326 A1 | 10/2002 | Fremy |
| 2002/0182263 A1 | 12/2002 | Stenti et al. |
| 2003/0017183 A1 | 1/2003 | Pollock |
| 2003/0032616 A1 | 2/2003 | Moskowitz et al. |
| 2003/0082321 A1 | 5/2003 | Kennedy et al. |
| 2003/0085170 A1 | 5/2003 | Scranton et al. |
| 2003/0108810 A1 | 6/2003 | Williamson et al. |
| 2003/0118672 A1 | 6/2003 | McPeak et al. |
| 2003/0133959 A1 | 7/2003 | Shacknai et al. |
| 2003/0152862 A1 | 8/2003 | Williamson et al. |
| 2003/0157006 A1 | 8/2003 | Hei et al. |
| 2003/0167033 A1 | 9/2003 | Chen et al. |
| 2003/0190266 A1 | 10/2003 | Tsurumi |
| 2003/0203009 A1 | 10/2003 | MacDonald |
| 2003/0203484 A1 | 10/2003 | Black et al. |
| 2004/0016410 A1 | 1/2004 | Riddles |
| 2004/0039066 A1 | 2/2004 | Crea |
| 2004/0048376 A1 | 3/2004 | Chabot et al. |
| 2004/0057972 A2 | 3/2004 | Shacknai et al. |
| 2004/0074212 A1 | 4/2004 | Yachi et al. |
| 2004/0081673 A1 | 4/2004 | Rayner et al. |
| 2004/0082667 A1 | 4/2004 | McCadden et al. |
| 2004/0086888 A1 | 5/2004 | Kornblith et al. |
| 2004/0087669 A1 | 5/2004 | Hausmanns et al. |
| 2004/0115818 A1 | 6/2004 | Puri et al. |
| 2004/0131806 A1 | 7/2004 | Barmore et al. |
| 2004/0137136 A1 | 7/2004 | Zheng et al. |
| 2004/0151826 A1 | 8/2004 | Milligan |
| 2004/0154220 A1 | 8/2004 | Holcomb |
| 2004/0156742 A1 | 8/2004 | Milan et al. |
| 2004/0157802 A1 | 8/2004 | Horwitz et al. |
| 2004/0186316 A1 | 9/2004 | Choudary et al. |
| 2004/0197339 A1 | 10/2004 | Brown |
| 2004/0213755 A1 | 10/2004 | Hochwalt et al. |
| 2004/0213774 A9 | 10/2004 | Till |
| 2004/0219126 A1 | 11/2004 | Seto et al. |
| 2004/0242818 A1 | 12/2004 | Williamson et al. |
| 2004/0265291 A1 | 12/2004 | Drake et al. |
| 2005/0025840 A1 | 2/2005 | Revnolds |
| 2005/0031651 A1 | 2/2005 | Gervais et al. |
| 2005/0031761 A1 | 2/2005 | Brucker et al. |
| 2005/0035062 A1 | 2/2005 | Hiltzik et al. |
| 2005/0054875 A1 | 3/2005 | Hei et al. |
| 2005/0058630 A1 | 3/2005 | Harris et al. |
| 2005/0069598 A1 | 3/2005 | Ribnicky et al. |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084474 A1 | 4/2005 | Wu et al. |
| 2005/0092070 A1 | 5/2005 | Bhatti |
| 2005/0092761 A1 | 5/2005 | Marganski et al. |
| 2005/0095653 A1 | 5/2005 | Goldstein et al. |
| 2005/0112085 A1 | 5/2005 | MacDonald et al. |
| 2005/0112176 A1 | 5/2005 | Dopson et al. |
| 2005/0112177 A1 | 5/2005 | Dopson et al. |
| 2005/0115895 A1 | 6/2005 | Simpson et al. |
| 2005/0136082 A1 | 6/2005 | Soane et al. |
| 2005/0136125 A1 | 6/2005 | Roth |
| 2005/0142096 A1 | 6/2005 | Wegner |
| 2005/0147692 A1 | 7/2005 | Roth |
| 2005/0158406 A1 | 7/2005 | McPeak et al. |
| 2005/0158424 A1 | 7/2005 | Nakano et al. |
| 2005/0169826 A1 | 8/2005 | Li |
| 2005/0176778 A1 | 8/2005 | Vermeer |
| 2005/0181048 A1 | 8/2005 | Romero |
| 2005/0182076 A1 | 8/2005 | Pacheco et al. |
| 2005/0187124 A1 | 8/2005 | Li et al. |
| 2005/0191343 A1 | 9/2005 | Liang |
| 2005/0215515 A1 | 9/2005 | Bucolo et al. |
| 2005/0222275 A1 | 10/2005 | Gabizon et al. |
| 2005/0224409 A1 | 10/2005 | Harshman et al. |
| 2005/0226827 A1 | 10/2005 | Ho |
| 2005/0227910 A1 | 10/2005 | Yang et al. |
| 2005/0260306 A1 | 11/2005 | Baldus |
| 2005/0261257 A1 | 11/2005 | Vermeer |
| 2005/0265979 A1 | 12/2005 | Aoki et al. |
| 2005/0266064 A1 | 12/2005 | McCarthy |
| 2005/0281883 A1 | 12/2005 | Daniloff et al. |
| 2006/0003069 A1 | 1/2006 | Zheng et al. |
| 2006/0006120 A1 | 1/2006 | Chen et al. |
| 2006/0006121 A1 | 1/2006 | Simpson et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0052438 A1 | 3/2006 | Ho et al. |
| 2006/0127508 A1 | 6/2006 | Larkins |
| 2006/0166948 A1 | 7/2006 | Vermeer |
| 2006/0177398 A1 | 8/2006 | McCook et al. |
| 2006/0194759 A1 | 8/2006 | Eidelson |
| 2006/0210646 A1 | 9/2006 | Oku et al. |
| 2006/0281822 A1 | 12/2006 | Appleton |
| 2007/0025950 A1 | 2/2007 | Elson |
| 2007/0028772 A1 | 2/2007 | Jain et al. |
| 2007/0048386 A1 | 3/2007 | Mallozzi, Sr. et al. |
| 2007/0180544 A1 | 8/2007 | Taylor et al. |
| 2007/0183936 A1 | 8/2007 | Newsam et al. |
| 2007/0243146 A1 | 10/2007 | Klock |
| 2007/0264212 A1 | 11/2007 | Ho |
| 2007/0270358 A1 | 11/2007 | Paoliambrosi |
| 2007/0292493 A1 | 12/2007 | Brierre |
| 2008/0038219 A1 | 2/2008 | Mosbaugh et al. |
| 2008/0076831 A1 | 3/2008 | Goetz |
| 2008/0102107 A1 | 5/2008 | Lewellyn et al. |
| 2008/0146458 A1 | 6/2008 | Hollingsworth et al. |
| 2008/0193427 A1 | 8/2008 | Kaesler et al. |
| 2008/0228161 A1 | 9/2008 | Claussen et al. |
| 2008/0249082 A1 | 10/2008 | Hollander |
| 2008/0251081 A1 | 10/2008 | Claussen et al. |
| 2008/0260871 A1 | 10/2008 | Fruitman |
| 2008/0274153 A1 | 11/2008 | Farmer |
| 2008/0275015 A1 | 11/2008 | Potter |
| 2008/0300311 A1 | 12/2008 | Kisak et al. |
| 2008/0317680 A1 | 12/2008 | Dueva-Koganov et al. |
| 2008/0319092 A1 | 12/2008 | Singh |
| 2009/0215888 A1 | 8/2009 | Jagat et al. |
| 2009/0312273 A1 | 12/2009 | De La Torre |
| 2009/0324784 A1 | 12/2009 | McLellan et al. |
| 2011/0105623 A1 | 5/2011 | Benjamin et al. |
| 2011/0136210 A1 | 6/2011 | Benjamin et al. |
| 2011/0203583 A1 | 8/2011 | Cozean et al. |
| 2011/0203585 A1 | 8/2011 | Cozean et al. |

FOREIGN PATENT DOCUMENTS

| | | |
|---|---|---|
| EP | 0827744 | 3/1998 |
| EP | 0976726 | 2/2000 |
| GB | 2028162 | 12/1979 |
| JP | 2005330199 | 12/2005 |
| WO | WO 85/00108 | 1/1985 |
| WO | WO 94/05272 | 3/1994 |
| WO | WO/95/03753 | 2/1995 |
| WO | WO 00/64868 | 11/2000 |
| WO | WO 01/73096 | 10/2001 |
| WO | WO 03/015760 | 2/2003 |

| | | |
|---|---|---|
| WO | WO 03/101415 | 12/2003 |
| WO | WO 2004/064877 | 8/2004 |
| WO | WO 2004/093541 | 11/2004 |
| WO | WO 2005/054553 | 6/2005 |
| WO | WO 2005/115546 | 12/2005 |
| WO | WO 2005/117913 | 12/2005 |
| WO | WO 2006/129149 | 12/2006 |
| WO | WO 2006/0135854 | 12/2006 |
| WO | WO 2007/009245 | 1/2007 |
| WO | WO 2007/016766 | 2/2007 |
| WO | WO/2007/0033082 | 3/2007 |
| WO | WO 2007/033082 | 3/2007 |
| WO | WO 2007/033083 | 3/2007 |
| WO | WO/2007/033083 | 3/2007 |
| WO | WO 2007/033180 | 3/2007 |
| WO | WO 2007/056205 | 5/2007 |
| WO | WO 2007/098591 | 9/2007 |
| WO | WO 2007/126191 | 11/2007 |
| WO | WO 2008/049020 | 4/2008 |
| WO | WO 2008/098871 | 8/2008 |
| WO | WO 2010/054093 | 5/2010 |
| WO | WO 2010/062721 | 6/2010 |
| WO | WO/2010/062721 | 6/2010 |
| WO | WO 2011/053848 | 5/2011 |
| WO | WO 2011/053854 | 5/2011 |
| WO | WO 2011/123695 | 10/2011 |

OTHER PUBLICATIONS

Baer P, Thomas L, Shainhouse JZ. Treatment of osteoarthritis of the knee with a topical diclofenac solution: a randomized, controlled 6-week trial. BMC Musculoskeletal Disord. 2005; 6:44.

Barrager, et al. A Multicentered, Open-Label Trial on the Safety and Efficacy of Methylsulfonylmethane in the Treatment of Seasonal Allergic Rhinitis, The Journal of Alternative and Complementary Medicine, vol. 8, No. 2, 2002, pp. 167-173.

Berry et al. *Natural Gas Odorants Desulfurization*, (2004) AIChE Annual National Meeting, Austin, Texas, Nov. 7-12.

Blumenthal L, Fuchs M. *The Clinical Use of Dimethyl Sulfoxide on Various Headaches, Musculoskeletal and Other General Medical Disorders*. Annals New York Academy of Sciences 1967:572-585.

Bookman A, Williams S, Shainhouse J. *Effect of a topical diclofenac solution for relieving symptoms of primary osteoarthritis of the knee: a randomized controlled trial*. CMAJ Aug. 17, 2004; 171(4):333-338.

Brayton CF. *Dimethyl Sulfoxide (DMSO); A Review*. The Cornel Veterinarian. Jan. 1986; 76(1):61-90.

Brechner V, Cohen D, Pretsky I. *Dermal Anesthesia by the Topical Application of Tetracaine Base Dissolved in Dimethyl Sulfoxide*, Annals New York Academy of Sciences. 1967:524-531.

Brien et al. *Systematic review of the nutritional supplements dimethyl sulfoxide (DMSO) and methylsulfonylmethane (MSM) in the treatment of osteoarthritis*. Osteoarthritis and Cartilage (2008) 16:1277-1288.

Brien S, Prescott P, Lewith G. *Meta-analysis of the Related Nutritional Supplements Dimethyl Sulfoxide and Methylsulfonlymethane in the Treatment of Osteoarthritis of the Knee*. eCAM Advance Access published May 27, 2009 in 10 pages.

Brown JH. *Clinical Experience with DMSO in Acute Musculoskeletal Conditions, Comparing a Noncontrolled Series with a Controlled Double Blind Study*. Ann NY Acad Sci 1967; 141(1):496-505.

Cherian L, Robertson C. *L-Arginine and Free Radical Scavengers Increase Cerebral Blood Flow and Brain Tissue Nitric Oxide Concentrations after Controlled Cortical Impact Injury in Rats*. Journal of Neurotrauma, vol. 20, No. 1, 2003; (Jan. 2003), pp. 77-85.

Debi R, et al. *The Role of MSM in Knee Osteoarthritis: A Double Blind, RandomizedProspective Study*. Osteoarthritis and Cartilage (2008) 15 Supplemental C:C231 (426).

Demos C et al. *Dimethyl Sulfoxide in Musculoskeletal Disorders*. Ann NY Acad Sci 1967:517-523.

Eberhardt et al. *DMSO in patients with Active Gonarthrosis. A double-blind, placebo-controlled Phase III Study*. Fortschr Med, Nov. 10, 1995: 113(31):446-450.

Evans MS, Reid KH, Sharp JB. *Dimethylsulfoxide (DMSO) blocks conduction in peripheral nerve C fibers: a possible mechanism of analgesia*. Neuroscience Letters, 150 (1993):145-148.

Feldman WE, Punch JD, Holden PC. *In vivo and in vitro effects of dimethyl sulfoxide on streptomycin-sensitive and-resistant Escherichia coli*. Ann NY Acad Sci, Jan. 27, 1975; 243:269-77.

Florain, The Solid State Structures of the Dimethylformamide and Dimethylsulfoxide Complexes of Dioxodichloromolybdenum (VI), ProQuest, 30-07B (1969), pp. 66.

Glasser D. *Dimethylsulfoxide (DMSO) "resensibilization" as potential chemotherapy for opportunistic mycobacterial disease*. Am Rev Respir Dis. Nov. 1978; 118(5):969-70.

Gorbach IN, Samtsov VS. *Therapeutic possibilities of inhalation of rifampicin with dimexide in phthisiopulmonology*. Probl Tuberk. 1991; (3):34-6.

Haigler HJ et al. *Comparison of the Analgesic Effects of Dimethyl Sulfoxide and Morphine*, Ann NY Acad Sci 1983; (411):19-27.

Hasegawa T, *Suppressive Effects of Methylsulfonylmethane (MSM) on Type II Collagen-induced Arthritis in DBA/1J Mice*. Jpn Pharmacol Ther 2004; 32 (7):421-427.

Jacob S, Appleton J. *MSM: The Definitive Guide*—Chapter 6, 45-54, Part II, Chapter 7, 57-68, Chapter 8, 69-76, Chapter 10, 84-90, Chapter 21, 181-186. California: Freedom Press, 2003.

Jacob S, Lawrence R, Zucker M, *The Miracle of MSM—The Natural Solution for Pain*. New York: Library of Congress Cataloging-in-Publication Data, 1999.

Jacob SW, Herschler R. *Pharmacology of DMSO*, Cryobiology, 1985, 23(1):14-27.

Jacob, S.W. and Wood, D.C. *Dimethyl sulfoxide (DMSO): Toxicology, pharmacology, and clinical experience*. Am. J. Surg. 1967; 114(3):414-426.

Jacob et al., Interstitial Cystitis Network—Char Log, Topic: Understanding DMSO; Mar. 28, 2000; The IC Network.

Jagannath C, Reddy VM, Gangadharam PR. *Enhancement of drug susceptibility of multi-drug resistant strains of Mycobacterium tuberculosis by ethambutol and dimethyl sulphoxide*. J Antimicrob Chemother. Mar. 1995; 35(3):381-90.

Jimenez RA, Willkens RF. *Dimethyl Sulphoxide: a perspective of its use in rheumatic diseases*. J Lab Clin Med 1982; 100(4):489-500.

John, H., Laudahn, G. *Clinical Experiences with the Topical Application of DMSO in Orthopedic Diseases: Evaluation of 4,180 Cases*, Annals New York Academy of Sciences, 1967; vol. 141:506-516.

Karlson AG, Ulrich JA, *Stock solutions of rifampin remain stable in dimethylsulfoxide for at least 8 months*, Appl Microbiol. Oct. 18, 1969(4):692-3.

Kim, et al. *Efficacy of Methylsulfonylmethane (MSM) in Osteoarthritis Path of the Knee: A Pilot Clinical Trial*. Osteoarthritis and Cartilage (2006) 14:286-294.

Knowles R. *Clinical Experience with DMSO in Small Animal Practice*, Annals New York Academy Sciences (1967) 141:478-483.

Koenen NJ, Haag RF, BiaP, RoseP. *Perkutane therapie bei aktivierter Gonarthrose*. Munch Med Wochenschr 1996; 138 (31-32):534-538.

Kubota et al. *Beneficial effect of L-Arginine for Stroke-like episode in MELAS* Brain and Development, Amsterdam, JL, vol. 26, No. 7, Oct. 1, 2004; pp. 481-483.

Liubinets VI, Kruk MV. *Dimexide in the treatment of endobronchitis in patients with destructive forms of pulmonary tuberculosis*, Zh Ushn Nos Gorl Bolezn. Nov.-Dec. 1969; 29(6):68-71.

Lockie and Norcross. *A Clinical Study on the Effects of Dimethyl Sulfoxide in 103 Patients with Acute and Chronic Musculoskeletal Injuries and Inflammations*, Annals New York Academy Sciences (1967) 141:599-602.

Martin D. and Hauthal H., *Dimethyl Sulfoxide*—Chapter 12. New York: John Wiley & Sons, 1971.

Matsumoto, J. *Clincal Trials of Dimethyl Sulfoxide in Rheumatoid Arthritis Patients in Japan*, Annals New York Academy Sciences. 1967; vol. 141:560-568.

Mitinskaia LA, Iukhimenko NV, Kamaeva VF. *BCG vaccination and increasing the effectiveness of treatment of post-vaccination complications by the use of rifampicin and dimexide*. Probl Tuberk. 1994; (5):4-7.

Mohamaddi F, O'Mara K, Unusual Patient Odor Interfering with Care, Resurrection Medical Center, Chicago, Ill. (1996).

Muller U, Urbanczik R. *Influence of dimethyl sulfoxide (DMSO) on restoring sensitivity of mycobacterial strains resistant to chemotherapeutic compounds*, J Antimicrob Chemother. May 1979; 5(3):326-7.

Murav'ev IuV, Venikova MS, Peskovskaia GN, Riazantseva TA, Sigldin IaA. *Effect of dimethylsulphoxide and dimethyl sulfone*. Patol Fiziol Eksp Ter Mar.-Apr. 1991; (2):37-39.

Nash DR, Steingrube VA. *In vitro drug sensitivity of M. avium-intracellulare complex in the presence and absence of dimethyl sulfoxide*. Microbios. 1982; 35(140):71-8.

Oshima Y, Theodosakis J, Amiel D. *The Effect of Distilled Methylsulfonylmethane (MSM) on Human Chondrocytes in vitro*. World Congress on Osteoarthritis, Ft. Lauderdale, Florida; Osteoarthritis and Cartilage 2007; vol. 15 Supplemental C123:213.

Ostojic et. al. *Laboratory Testing of Cabin Air Filters for the Removal of Reduced-Sulfur Odors*. New Engine Design and Automotive Filtration SAE Special Publications 1998; 1362:41-58.

Paul M. *Interval Therapy with Dimethyl Sulfoxide*. Ann NY Acad Sci Mar. 1967; 1(141):586-598.

Paulus E. *FDA advisory committee meeting: methotrexate; guidelines for the clinical evaluation of anti-inflammatory drugs; DMSO in scleroderma*. Arthritis & Rehumatism Oct. 1986; 10(29):1289-1290.

Pennsaid Monograph, Nuvo Research, 2010.

Penrod, D., Bacharach, B., Templeton, J. *Dimethyl Sulfoxide for Incisional Path after Thoracotomy: Preliminary Report*. Annals New York Academy Sciences Mar. 15, 1967; vol. 141(1):493-495.

Potzz GE, Rampey JH, Bejamin F. *The effect of dimethyl sulfoxide (DMSO) on antibiotic sensitivity of a group of medically important microorganisms: preliminary report*. Ann NY Acad Sci. Mar. 15, 1967; 141(1):261-72.

Robertson et al. "*L-Arginine reduces neuronal damage after traumatic brain injury in the mouse*" Journal of Neurotrauma, vol. 17, No. 10, Oct. 2000, p. 945.

Ropek M, Pawlowska I, Szydlowska T. *Effects of dimethyl sulfoxide on tubercle bacilli resistant to INH*. Gruzlica. Aug. 1971; 39(8):738-41.

Rosenbaum WM, Rosenbaum EE, Jacob S. The use of dimethyl sulfoxide (DMSO) for the treatment of intractable pain in surgical patients. Surgery 1965: 58.

Roth SH, Shainouse JZ, Efficacy of Safety of a topical diclofenac solution (Pennsaid) in the treatment of primary osteoarthritis of the knee: a randomized, double-blind, controlled clinical trial. Arch Intern Med. Oct. 11, 2004;164(18):2017-23.

Seibert F, Farrelly F, Shepherd C. *DMSO and other combatants against bacteria isolated from leukemia and cancer patients*. Ann NY Acad Sci Mar. 1967; 1(141):175-201.

Shainhouse JZ, Grierson L, Naseer Z, A long-term, open-label study to confirm the safety of topical diclofenac solution containing dimethyl sulfoxide in the treatment of the osteoarthritic knee, American Journal of Therapeutics 0(0) 2010.

Shaklee Health Network, "Methyl Sulfonyl Methane," [online], 2006 [retrieved on Dec. 16, 2010]. Retrieved from the internet: <URL:http://content.hbiondemand.com/shap/monoVMN.asp?objID=100028]: p. 1-4, especially p. 1, para 1 to p. 2, para 1.

Simon L, et. al. *Efficacy and Safety of Topical Diclofenac containing Dimethyl Sulfoxide (DMSO) compared with those of Topical Placebo, DMSO Vehicle and Oral Diclofenac for Knee Osteoarthritis*. Pain, 143(2009):238-245.

Smith G, Bertone AL, Kaeding C, et al. *Anti-Inflammatory effects of topically applied dimethyl sulphoxide gel on endotoxin-induced synovitis in horses*. Am J Vet Res Sep. 1998; 59(9):1149-52.

Steinberg, A. *The employment of DMSO as an anti-inflammatory agent and steroid transporter in diversified clinical diseases*. Ann NY Acad Sci 1967, 141(1):532-550.

Szydlowska T. *In Vitro and in Vivo Studies on the role of Dimethylsulfoxide (DMSO) in Resensibilization of Bacterial Strains Resistant to Antibiotics and Chemotherapeutic Agents*. Zbl. Bakt. Hyg., I. Abt. Orig. A 239, 270-274 (1977).

Szydlowska T, Pawlowska I. *Comparative Studies on the Influence of Dimethylsulfoxide (DMSO) on Reversion to Sensitivity to Isonicotinic Acid Hydrazide (INH) and Rifampicin (RMP) in Resistant Strains of Tubercle bacilli*. Arch Immunol Ther Exp (Warsz). 1976; 24(4):575-77.

Szydlowska T, Pawlowska I. *In vivo studies on reversion to sensitivity of INH-resistant tubercle bacilli under the influence of dimethylsulfoxide (DMSO)*. Arch Immunol Ther Exp (Warsz). 1974; 22(4):559-61.

Szydlowska T. *Studies on the role of dimethylsulfoxide in resensibilization of antibiotic-resistant bacterial strains*. Arch Immunol Ther Exp (Warsz). 1972; 20(2):193-202.

Szydlowska T. *Studies on the role of dimethylsulfoxide in resensibilization of bacterial strains resistant to sulfonamides*. Arch Immunol Ther Exp (Warsz). 1972; 20(2):203-207.

Teigland MB, Saurino V. *Clinical Evaluation of Dimethyl Sulfoxide in Equine Applications*. Ann NY Acad Sci Mar. 1967; 141(1):471-7.

Tugwell PS, Wells GA, Shainhouse JZ. Equivalence study of a topical diclofenac solution (Pennsaid) compared with oral diclofenac in symptomatic treatment of osteoarthritis of the knee: a randomized, controlled trial. J Rheumatol. Oct. 2004; 31(10):1893-5.

Usha PR, Naidu MUR. *Randomized, double-blind, parallel, placebo-controlled study of oral glucosamine, methylsulfonylmethane and their combination in osteoarthritis*. Clin Drug Invest 2004; 24(6):353-63.

Vuopala U, et. al. *The Analgesic action of DMSO ointment in arthrosis*. Acta Rheum Scand 1971; 17(1):57-60.

Wierzbicki, Homocysteine and cardiovascular disease: a review of the evidence; Diabetes and Vascular Disease Research; Jun. 2007; pp. 143-149; vol. 4, Iss 2; The British Library.

Wood, DC, Wood, J. *Pharmacologic and Biochemical Considerations of Dimethyl Sulfoxide*. Ann NY Acad Sci Jan. 1975; 243:7-19.

Zuckner, J. Uddin, J., Gantner, G. *Local Application of Dimethyl Sulfoxide and DMSO Combined with Triamcinolone Acetonide in Rheumatoid Arthritis*. Ann NY Acad. Sci. Mar. 1967; 1(141):555-9.

"Guidance on Medical Device Patient Labeling" accessed Mar. 10, 2010. http://www.fda.gov/MedicalDevices/DeviceRegulationandGuidance/GuidanceDocuments/ucm070782.htm.

Kocsis, et al., "Biological Effects of the Metabolites of Dimethyl Sulfoxide", Ann N. Y. Acad. Sci. 243, 104 09 (1975).

Scrubs, online encyclopedia article, accessed Mar. 10, 2010. http://en.wikipedia.org/wiki/Scrubs_(clothing).

SYSTEMS FOR REMOVING DIMETHYL SULFOXIDE (DMSO) OR RELATED COMPOUNDS, OR ODORS ASSOCIATED WITH SAME

RELATED APPLICATIONS

This application is a continuation of U.S. application Ser. No. 12/066,485, filed Mar. 11, 2008, which is the U.S. National Phase under 35 U.S.C. §371 of International Application No. PCT/US2006/035321, filed Sep. 11, 2006 (published as WO 2007/033083A1 and herein incorporated by reference), which claims priority to U.S. Provisional Application Ser. Nos. 60/716,271; 60/716,336; 60/716,278; and 60/716,369, all of which were filed Sep. 12, 2005, and are herein incorporated by reference.

BACKGROUND OF THE INVENTION

1. Field of the Invention

The present invention relates generally to materials for facilitating the administration of DMSO and associated compounds. In some embodiments, these materials comprises adsorbents for the removal of the odors and compounds resulting from the metabolism or degradation of DMSO and associated compounds. In other embodiments, these materials comprise clean air members and fabrics that absorb odors or compounds. In further embodiments, these materials comprise a clean air supply assembly for removing odors and compounds. In yet other embodiments, these materials comprises indicators to reveal the presence or absence of DMSO and associated compounds.

2. Description of the Related Art

Odors and chemicals resulting from the treatment of patients with DMSO and related compounds can be so oppressive as to diminish the effectiveness and receptiveness of the medical staff. Such odors may be likened to the smell of rotten eggs. New procedures are emerging which require the treatment of seriously ill persons by using far larger volumes of DMSO than at present. The resulting highly oppressive odors may emanate from any part of the patient's body. The capture of these odors can be crucial to the success of the new medical procedures.

At present, Applicant believes that there is no known effective method practiced for the removal of these noxious odors. Previous odor collecting disposables containing activated carbon for other applications have been directed toward specific bodily areas and fluids, but not for removal of metabolites of DMSO. In addition, the need for compact, easily positioned air cleaning devices has not been fully addressed. Currently, the intravenous administration of DMSO has been limited by side effects associated with the noxious odors. As DMSO becomes a much more routine drug of choice for the treatment of seriously ill or injured patients, the success of these treatment methods may well rest on the availability of highly effective air cleaning devices for the protection of the medical staff and visitors. In addition, at present, the only method known to Applicant for detection of these odorous compounds is human olfaction which can be undependable.

SUMMARY OF THE INVENTION

There is a need for compositions, devices, and methods for the removal of DMSO metabolites and related compounds which will remove these chemicals and/or their noxious odors, as well as indicators to determine the presence of these compounds.

The phrases "DMSO associated compounds", "associated compounds", or "related compounds" as used herein shall be given their ordinary meaning and shall include degradation compounds, derivatives, precursors, and metabolites of DMSO, such as methylsulfonylmethane (MSM or $DMSO_2$) and dimethyl sulfide or methylthiomethane (DMS).

Several embodiments of present invention relate to materials and methods for the removal of odors and chemicals resulting from the treatment of patients with DMSO and other compounds and chemicals. Also provided are modified polyamines, odor capturing fabrics which comprise these modified polyamines, items manufactured from these fabrics and methods of manufacture and use of the fabrics.

In one embodiment, the invention comprises an indicator for DMSO associated compounds, its method of manufacture, and an apparatus including the indicating material.

In another embodiment, the invention comprises a device to purify the air at a DMSO delivery or metabolism site. For example, a clean air device that removes DMSO metabolites and/or DMSO odors may be well-suited for hospital rooms where a patient is receiving DMSO or in a room where a patient is recovering after receiving DMSO therapy. In one embodiment, the clean air device comprises a portable, collapsible, adjustably directable clean air delivery supply assembly and enclosure for use in DMSO treated medical patient environments to provide localized clean air free of the odors, DMS, and/or compounds resulting from the metabolism of DMSO and DMSO associated compounds, including, but not limited to, hydrogen sulfide and potentially methyl mercaptan.

In one embodiment, it may be desirable to detect the presence of DMSO and associated compounds. Accordingly, in one embodiment, the invention comprises visual color indicators to detect the presence or absence of DMSO metabolites such as DMS.

In one embodiment, the invention comprises core particles that adsorb DMSO or related compounds, or the odors associated with said compounds.

In another embodiment, the invention comprises an adsorbent for adsorbing DMSO or related compounds, or the odors associated with said compounds. The adsorbent comprises an inner layer, an intermediate layer, and an outer layer. The inner layer comprises adsorbing core particles that adsorb DMSO or related compounds, or the odors associated with said compounds. The intermediate layer, which is optional, contacts the inner layer and the outer layer. The outer layer comprises a porous coating. In some embodiments, the adsorbent may reduce undesired pathogens and odors that are unrelated to DMSO.

In a further embodiment, the adsorbent comprises at least one indicator for indicating the presence of DMSO or related compounds. The indicator comprises permanganate in one embodiment. In one embodiment, the indicator is colored, and is adapted to decrease in color or intensity as DMSO or related compounds are removed. Thus, in one embodiment, color intensity can be correlated to the concentration of undesired compounds or odors. In other embodiments, different colors indicate different levels of undesired odors or compounds.

In one embodiment, the adsorbing core particles are selected from the group consisting of one or more of the following: activated carbon, an inorganic oxide, a compound having ion exchange capacity, an ion exchange resin, and a chemical deodorizer.

In one embodiment, the intermediate layer comprises a metal compound and a water-soluble organic material disposed between the core particles and the porous coating.

In one embodiment, the outer layer consists only of a porous coating. In other words, a porous coating is applied directly to the intermediate layer or to the core particles. In other embodiments, the outer layer comprises a layer of material which is additionally coated with a porous coating.

In another embodiment, the outer layer comprises a polymer selected from the group consisting of one or more of the following: a fluororesin, a polyamide resin, a polyimide resin, a polyester resin, a polystyrene resin, a polyolefin resin, a polycarbonate resin, a polysulfone resin, an acrylic resin, a cellulose resin, a vinyl chloride resin, a polyacetal resin, a polyurethane resin and a copolymer or derivative thereof. The polymer may also be selected from the group consisting of one or more of the following: polytetrafluoroethylene, polyhexafluoropropylene, polydifluoroethylene, polyvinylidene fluoride, polyvinyl fluoride, and a copolymer or derivative thereof.

In one embodiment, the porous coating has a thickness of about 0.01 µm to about 1,000 µm, an average pore diameter of about 0.01 µm to about 500 µm, and/or a porosity of about 3% to about 90%.

In a further embodiment, the invention comprises a method for removing DMSO metabolites, comprising contacting said metabolites with an adsorbent according to any one of the embodiments described herein. The DMSO metabolites may be produced by an individual receiving DMSO treatment. Alternatively, the DMSO metabolites may be degradation products caused by the exposure of DMSO to the environment (e.g., the air or a fluid).

In another embodiment, the invention comprises a method for removing odors associated with DMSO or related compounds, comprising exposing said odors to an adsorbent according to any one of the embodiments described herein.

In yet another embodiment, the invention comprises a clean air member for removal of DMSO or related compounds, or the odors associated with said DMSO or related compounds comprising adsorbent according to any one of the embodiments described herein.

In another embodiment, the invention comprises a clean air supply assembly for removal of DMSO or related compounds, or the odors associated with said DMSO or related compounds comprising adsorbent according to any one of the embodiments described herein.

In one embodiment, the invention comprises an apparatus for removing DMSO or related compounds, or the odors associated with said DMSO or related compounds from the exhaust outlet of a medical respiratory ventilator, wherein said apparatus comprises a gas scavenging device comprising the adsorbent of according to any one of the embodiments described herein. The gas scavenging device is optionally connected to said exhaust outlet.

In another embodiment, the invention comprises a face mask for reducing exposure of DMSO or related compounds, or the odors associated with said DMSO or related compounds comprising an adsorbent of according to any one of the preceding claims.

In another embodiment, the face mask filters out undesired odors that are unrelated to DMSO. The face mask may also filter airborne pathogens, including viruses and bacteria. The filtering of these other compounds may be in addition to or instead of the filtering of DMSO and associated compounds. The face mask may be a duckbill-type mask, and may comprise an exhale valve.

In one embodiment, the invention comprises a face mask comprising an outer shield layer comprising a synthetic fiber; a copper layer comprising a fiber and powdered copper; a carbon layer comprising a fiber and activated carbon; a chemical layer comprising a fiber and one or more, odor absorbing chemicals; and a facial layer comprising a synthetic fiber. The face mask may contain less than the layers described herein, or may comprise additional layers. The multi-layered face mask may protect a user from pathogens and/or DMSO compounds.

DETAILED DESCRIPTION OF THE PREFERRED EMBODIMENT

Several embodiments of the present invention relates generally to materials for facilitating the administration of DMSO and associated compounds. In some embodiments, these materials comprises adsorbents for the removal of the odors and compounds resulting from the metabolism or degradation of DMSO and associated compounds. In other embodiments, these materials comprise clean air members and fabrics that absorb odors or compounds. In further embodiments, these materials comprise a clean air supply assembly for removing odors and compounds. In yet other embodiments, these materials comprises indicators to reveal the presence of these compounds.

Adsorbents

In one embodiment, the invention comprises an adsorbent adapted for the partial or complete removal of the metabolites of DMSO and other compounds, and/or related odors.

In one embodiment, the adsorbent material comprises three layers: an inner layer; an intermediate layer, and an outer layer. In another embodiment, the adsorbent material may comprise one, two, or three of the layers described above. In other embodiments, additional layers are provided. Layers can be fixed or otherwise coupled to one another or to other materials (using, for example, adhesives, sealants, stitches, etc).

In one embodiment, the inner layer comprises core particles containing at least one adsorbing material.

In one embodiment, the intermediate layer comprises at least one porous coating layer including a polymer material that coats the core particles. The intermediate layer may comprise a metal compound and a water-soluble organic material disposed between the core particles and a porous coating layer. The water-soluble organic material is selected from the group consisting of one or more of the following: polymers of sugar, cellulose derivatives, alginic acid, methacrylic acid, acrylic acid, vinylpyrrolidone, vinyl alcohol, oxyolefins, and organic sulfur oxides such as $DMSO_2$ (dimethyl sulfone).

In one embodiment, the outer layer comprises a coating, such as a porous coating layer. In one embodiment, the coating layer may be formed by spraying and applying a suspension or a solution containing a polymer material over the adsorbing material, or by immersing the adsorbing material into the suspension or the solution.

In one embodiment, an adsorbent according to any one of the embodiments described herein preferentially absorbs DMS is provided. In another embodiment, the adsorbent preferentially adsorbs MSM. In other embodiments, the adsorbent adsorbs all odor causing compounds related to DMSO.

The layers, according to some embodiments of the invention, are described below.

The Inner Layer of the Adsorbent

Figure 1:
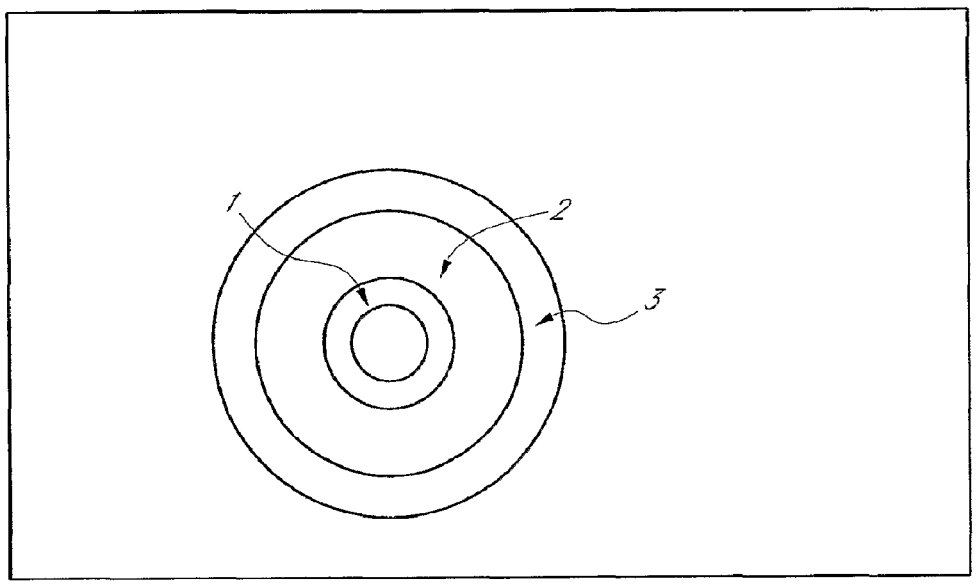
FIG. 1 shows an adsorbent according to one embodiment of the invention.

In one embodiment, a material for adsorbing DMSO and associated compounds, and/or the odors related to same comprises an inner layer. FIG. 1 shows the adsorbent material according to one embodiment of the invention. In one embodiment, the inner layer 1 comprises core particles. The core particles may or may not represent the entire adsorbent material and may comprise one or more of the following: activated carbon, an inorganic oxide, a compound having ion exchange capacity, a modified compound thereof, an ion exchange resin, a chemical deodorizer, silica gel, alumina gel, zeolite, a molecular sieve, diatomaceous earth, inorganic oxide (e.g., copper oxide, iron oxide), chitosan, dextran sulfate, polyallylamine, sulfonated polystyrene resins, polyacrylic acid, polymethacrylic acid or a derivative thereof. Combinations of two or more of these compounds are used in some embodiments.

In one embodiment, the compound having ion exchange capacity is selected from the group consisting of one or more of the following: chitosan, dextran sulfate, polyallylamine, sulfonated polystyrene resins, polyacrylic acid, polymethacrylic acid and a derivative thereof.

Mechanisms of adsorption include chemical oxidation or reduction and/or mechanical entrapment. Thus, in one embodiment, the inner layer is an adsorbent that comprises core particles, which adsorb odors or compounds by physically trapping, enclosing, or isolating said odors and compounds. In another embodiment, the inner layer is an adsorbent that comprises core particles, which adsorb odors or compounds by chemically oxidizing or reducing said odors and compounds. In yet another embodiment, undesired odors and compounds are reduced or eliminated because the core particles chemically react with said odors and compounds to render them inert or inactive.

In one embodiment, the core particles have an average particle size of about 0.01 mm to about 100 mm. In one embodiment, the inner layer has a thickness of about 0.1 μm to 1,000 μm. In certain embodiments relating to use of the core particles as an indicator, greater size may provide greater absorbency but lesser sensitivity, and lower size may give inadequate visual indication.

In one embodiment, the core particles are formed by a tableting process.

In one embodiment, the inner layer comprises core particles that are coated. This coating can be the same or different than the outer layer. In one embodiment, the core particles have a porous coating layer having an average pore size of 0.001 μm to 50 μm.

In another embodiment, the core particles are fixed on or otherwise coupled to a member having a one-dimensional structure or a two-dimensional structure. In one embodiment, the core particles are fixed onto the member having the two-dimensional structure at a density of about 0.1 to about 100,000 particles per 1 $cm^2$ of a surface of said member having the two-dimensional structure.

In one embodiment, the particles having said porous coating layer formed thereon are fixed on one surface of said member having the two-dimensional structure, and an adhesive is applied on another surface of said member having the two-dimensional structure.

In one embodiment, the particles having said porous coating layer formed thereon are fixed on a member having a three-dimensional structure. In a preferred embodiment, the core particles are fixed onto said three-dimensional structure at a density of about 1 to about 1,000,000 particles per 1 $cm^3$ of a volume of said member having the three-dimensional structure.

In one embodiment, the core particles having said porous coating layer formed thereon are fixed to a member in a state of a layer having a thickness of a single particle to about 1,000 particles. In certain embodiments relating to use as a visual indicator, greater density may provide greater adsorbency but lesser sensitivity, and lower density may give inadequate visual indication at some point.

In one embodiment, the core particles having said porous coating layer formed thereon are fixed to the member with an adhesive. The adhesive may comprise an organic solvent type adhesive, a water type adhesive, a hot melt type adhesive, or combinations thereof. The member may comprise a portion covered by an air permeable sheet. The member may be entirely wrapped with an air permeable sheet. The member may be contained in an air permeable container. The air permeable container may comprise an unwoven cloth, a woven cloth, a mesh, a net, or combinations thereof.

In one embodiment, the core particles having said porous coating layer formed thereon are wrapped with an air permeable sheet. In one embodiment, the core particles having said porous coating layer formed thereon are contained in the air permeable sheet in a number of about 1 to about 100,000,000. In certain embodiments, greater density may provide greater adsorbency but lesser sensitivity, and lower density may give inadequate visual indication.

In certain embodiments relating to use of the core particles as an indicator, greater size may provide greater adsorbency but lesser sensitivity, and smaller size may give inadequate visual indication at some point.

The Intermediate Layer of the Adsorbent

In one embodiment, a material for adsorbing DMSO and associated compounds, and/or the odors related to same comprises an intermediate layer. FIG. 1, reference numeral 2 shows the intermediate layer according to one embodiment of the invention. The intermediate layer of the adsorbent may comprise one or more of the following: the oxide, hydroxide, carbonate, sulfates, phosphate, metasilicate, borate, oxalate, tungstate, molybdate, vanadate, chromate, selenate, and manganate of a metal or the metal itself. The metal may also include titanium, zirconium, silicon, zinc, iron, manganese, aluminum, magnesium, nickel, copper, silver, barium, calcium, scandium, bismuth, molybdenum, niobium, neodymium, antimony, selenium, stannum, strontium, terbium, tellurium, thorium, and yttrium.

In another embodiment, the metal compound has a particulate shape having an average particle size of about 0.001 μm to about 50 μm Other shapes and sizes may be used.

In one embodiment, the intermediate layer has a thickness of about 1 μm to about 10,000 μm. In one embodiment, the greater number lending toward more adsorbency but less efficiency of coating use while the lower number contributes to high efficiency of coating use but lower volumetric adsorbency. In certain embodiments, too thin a coating may result in poor indication due to lack of color, and too thick a coating may result in too much adsorption and loss of sensitivity.

The Outer Layer of the Adsorbent

In one embodiment, a material for adsorbing DMSO and associated compounds, and/or the odors related to same comprises an outer layer. FIG. 1, reference numeral 3 shows the outer layer (e.g., porous material) according to one embodiment of the invention. The outer lay may comprises a porous coating layer. The outer layer may comprise one or more of the following: a fluororesin, a polyamide resin, a polyimide resin, a polyester resin, a polystyrene resin, a polyolefin resin, a polycarbonate resin, a polysulfone resin, an acrylic resin, a cellulose resin, a vinyl chloride resin, a polyacetal resin, a polyurethane resin and a copolymer thereof, and a derivative thereof or polytetrafluoroethylene, polyhexafluoropropylene, polydifluoroethylene, polyvinyliden fluoride, polyvinyl fluoride, and a copolymer or derivative thereof. Combinations of two or more of these materials are used in some embodiments.

In one embodiment, the porous coating layer has a thickness of about 0.01 μm to about 1,000 μm. In one embodiment, the greater number lending toward more adsorbency but less efficiency of coating use while the lower number contributes to high efficiency of coating use but lower volumetric adsorbency.

In one embodiment, the porous coating layer has an average pore diameter of about 0.01 μm to about 500 μm and/or has a porosity of about 3% to about 90%. In one embodiment, the porous coating layer is colored.

In one embodiment, a method for producing the adsorbent, or indicating adsorbent, is provided. In a preferred embodiment, the method comprises forming the coating layer by applying a liquid containing said polymer material onto a surface of said core particles. The coating layer may be formed by spraying said liquid over said core particles and/or immersing said core particles into said liquid. In one embodiment, the liquid comprises a suspension of said polymer material and/or a solution of said polymer material.

In one embodiment, during said step of forming the coating layer or after said step of forming the coating layer, at least one of a step of heating and a step of decreasing a pressure is carried out to draw said porous coating layer.

In one embodiment, during said step of forming the coating layer or after said step of forming the coating layer, a heating process is carried out so that said coating layer partially shrinks and partially expands.

In one embodiment, the core particles in said step of forming the coating layer are in a water-containing state, in an oil-containing state, or in a frozen state thereof.

In one embodiment, the liquid comprises a pore-forming agent. The pore-forming agent may comprise a water-soluble polymer or oligomer. The water-soluble polymer or oligomer may be selected from the group consisting of one or more of the following: cellulose, poly(oxyolefin), polyvinylpyrrolidone, polyvinyl alcohol, a saponification compound of polyvinyl acetate, polyacrylic acid, polymethacrylic acid, and derivatives thereof. In another embodiment, the water-soluble polymer or oligomer is selected from the group consisting of one or more of the following: methyl cellulose, hydroxymethyl cellulose, hydroxyethyl cellulose, hydroxypropyl cellulose, polyvinylpyrrolidone, polyvinyl alcohol, polyethylene glycol, polypropylene glycol, and derivative thereof.

In one embodiment, the pore-forming agent comprises an oil soluble polymer or oligomer. The oil soluble polymer may comprise liquid paraffin.

In one embodiment, the pore-forming agent is removed during or after the step of forming said coating layer. In another embodiment, the pore-forming agent is removed by one or more of the following processes: extraction, evaporation, sublimation or combustion.

In an alternative embodiment, the invention comprises a packed bed containing the adsorbent of one embodiment of the present invention. The packed bed, in some embodiments, functions as a holder for the adsorbent material. The packed bed of adsorbent may be incorporated into a cartridge for containment of the adsorbent material. The cartridge may be in the form of a rectangular, cylindrical or otherwise shaped vessel. The cartridge may be provided in conjunction with a device for introducing air into said rectangular, cylindrical or otherwise shaped vessel, wherein the adsorbent is partially or completely contacted when the air is introduced therein. One of skill in the art will understand that other shapes may also be used according to alternative embodiments of the invention.

Clean Air Member

In one embodiment of the invention, a device and method for cleaning air comprising contacting air with an indoor ambient air cleaning member (such as a cartridge or filter). In one embodiment, the clean air member comprises the adsorbent material described above. In one embodiment, the clean air member adsorbs DMSO and/or DMSO related compounds, and/or odors associated with same. In some embodiments, the clean air member additionally removes one or more undesired compounds from the air that are unrelated to DMSO (e.g., toxic fumes or gases).

In one embodiment, the clean air member (such as a cartridge or filter) comprises an inner layer, an intermediate layer, and an outer layer, as described above.

The clean air member may be contained in a rectangular, cylindrical or otherwise shaped vessel, and said indoor ambient air cleaning member is freely convected when the air is introduced therein. The vessel may be tilted.

In several embodiments of the invention, the clean air member according to any one of the embodiments described herein is an ambiance odor or sulfur chemical regulating member.

In one embodiment, the clean air member (such as a cartridge or filter) comprises core particles comprising at least one odor or sulfur chemical regulating material of an acid or acid salt, and a porous coating layer including a polymer material that coats the core particles. In one embodiment, the acid is selected from the group consisting of one or more of the following: lactic acid, malic acid, tartaric acid, oxalic acid, chromic acid, dichromic acid, manganic acid, permanganic acid, thiocyanic acid, cyanic acid, carbonic acid, hydrochloric acid, perchloric acid, chloric acid, chlorous acid, hypochlorous acid, hydriodic acid, periodic acid, iodic acid, iodous acid, hypoiodous acid, sulfuric acid, sulfurous acid, nitric acid, nitrous acid, and phosphoric acid.

In one embodiment, the clean air member comprises an odor or sulfur chemical regulating material selected from the group consisting of one or more of the following: sodium sulfate, an alkali metal salt of phosphoric acid, an alkali metal salt of hydrogenphosphate, an ammonium salt of phosphoric acid, and an ammonium salt of hydrogen phosphate.

In one embodiment, the clean air member comprises core particles that comprises a hydrophilic polymer compound. The hydrophilic polymer compound may be selected from the group consisting of one or more of the following: vinyl alcohol, vinylpyrrolidone, acrylic acid, methacrylic acid, a saponification compound of vinyl acetate, a cellulose ester, an oxyolefin, and a sugar.

In one embodiment, the clean air member comprises core particles that have an average particle size of about 0.01 mm to about 100 mm.

In one embodiment, the clean air member comprises core particles comprising at least one odor or sulfur chemical regulating material of an acid salt, and a porous coating layer comprising a polymer material that coats said core particles is provided. The acid salt may be selected from the group consisting of one or more of the following: an alkali metal salt, an alkaline earth metal salt, and an ammonium salt.

In one embodiment, the core particles further comprises a hydrophilic polymer compound. The hydrophilic polymer compound may be selected from the group consisting of one or more of the following: vinyl alcohol, vinylpyrrolidone, acrylic acid, methacrylic acid, a saponification compound of vinyl acetate, a cellulose ester, an oxyolefin, and a sugar.

In one embodiment, the clean air member comprises a porous coating layer having a thickness of about 0.1 μm to about 1,000 μm and/or average pore size of about 0.001 μm to about 50 μm. The porous coating layer of the clean air member may comprise a silver deposit layer.

In one embodiment, the clean air member comprises a porous coating layer that comprises material selected from the group consisting of one or more of the following: a fluororesin, a polyamide resin, a polyimide resin, a polyester resin, a polystyrene resin, a polyolefin resin, a polycarbonate resin, a polysulfone resin, an acrylic resin, a cellulose resin, a vinyl chloride resin, a polyacetal resin, a polyurethane resin, copolymers thereof, and derivative thereof. The porous coating layer may be colored.

In a further embodiment, an adsorbent for removal of respiratory exhalation from a patient treated with DMSO is provided. In yet another embodiment, an adsorbent for removal of DMSO metabolites from a respiratory ventilator or an isolation room ventilator is provided. The adsorbent may be part of the clean air member.

In one embodiment, the clean air member comprises an oxidizing agent. The oxidizing agent is selected from the group consisting of one or more of the following: a mixture of ascorbic acid and an iron-containing compound, permanganates, manganese dioxide, chromates, dichromates, osmium tetraoxide, ruthenium tetraoxide, silver oxide and palladium chloride. In one embodiment, the iron-containing compound is selected from the group consisting of one or more of the following: iron chloride, iron bromide, iron iodide, iron oxide, iron perchlorate, iron thiocyanate, iron sulfate, iron sulfide, iron acetate, iron oxalate, Mohr's salt, di-iron monophosphide and tri-iron monophosphide.

Fabrics

In several embodiments of the present invention, a fabric that reduces or eliminates the odor of DMSO and associated compounds is provided. In one embodiment, the fabric comprises odor adsorbing woven or non-woven fabric suitable for the manufacture of clothing, bedding and other protective items capable of the partial or complete capture of the metabolites of DMSO and others. Adsorption may include chemical oxidation, reduction, physical entrapment in fissures, or other means. The adsorbent fabric may include adsorbent fibers or fibers coated with an adsorbent or it may be layered with adsorbent material between the layers. Finally, the fabric may incorporate any or all of these modes of odor capture simultaneously.

In one embodiment, the fabric comprises a three dimensional web. In one embodiment, the basic fiber support structure of the three dimensional web comprises woven or non-woven web of the fibers of polyethylene, polypropylene, polyvinyl chloride, polyurethane, polyamide, nylon, polyacrilan, rayon, silk, ramey, cellulosic material and any other suitable fibrous material or material which may be made fibrous. Intermediate layers may comprise knit or randomly formed copper, aluminum, iron, glass, carbon, or other inorganic fibers. Each layer may be formed on a knitting, weaving, moving web, fluid dispersion, or other device. Layers may be combined following the forming of each or one or more layers may be formed as they are layered. Layers may be adhered together by crosslinking, hot melt stitching, sewing, gluing, or other methods well known in the art.

In one embodiment, the odor adsorbing fibers of the fabric may comprise a modified polyamine which comprises a hybrid inorganic/organic material comprising a polyamine and an inorganic oxide. The polyamine may comprise one or more of the following: amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups, poly(lysine), polyethylenimine, polyethylenimine derivatives, poly(vinylamine), polymers containing diallylamine, and polymers containing allylamine, amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups, poly(lysine), polyethylenimine, polyethylenimine derivatives, poly(vinylamine), polymers containing diallylamine, and polymers containing allylamine, amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups, poly(lysine), polyethylenimine, polyethylenimine derivatives, poly(vinylamine), polymers containing diallylamine, and polymers containing allylamine, amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups, polyethylenimine, polyethylenimine derivatives, poly(vinylamine), polymers containing diallylamine, and polymers containing allylamine or a nanostructured polyamine which comprises a polyamine reacted with one or more crosslinkers. MSM (methyl sulfonyl methane) adsorbents may also be included as coatings, admixtures of the above or alone. In one embodiment, MSM is both a metabolite of DMSO and used as an adsorbent. In this embodiment, the MSM used as the adsorbent is substantially odorless and can adsorb odorous DMS (which can be obtained from DMSO through reduction, potentially in an anaerobic metabolic environment), and other odorous compounds that result from DMSO metabolism. In embodiments where the two main metabolites of DMSO are DMS and MSM, exogenous MSM can be used as an adsorbent alone or in combination with other adsorbents. MSM may also be used to adsorb sulfur contain compounds that are related or unrelated to DMSO.

In one embodiment, the odor adsorbing coatings of the fibers, the cross linking members or the intermediate layers of a multilayer fabric may comprise one or more of the following: activated carbon, an inorganic oxide, a compound having ion exchange capacity, a modified compound thereof, an ion exchange resin, a chemical deodorizer, silica gel, alumina gel, zeolite, a molecular sieve, diatomaceous earth, copper oxide, iron oxide, chitosan, dextran sulfate, polyallylamine, sulfonated polystyrene resins, polyacrylic acid, polymethacrylic acid or a derivative thereof. Further, these odor adsorbing coatings may comprise a fluororesin, a polyamide resin, a polyimide resin, a polyester resin, a polystyrene resin, a polyolefin resin, a polycarbonate resin, a polysulfone resin, an acrylic resin, a cellulose resin, a vinyl chloride resin, a polyacetal resin, a polyurethane resin and a copolymer thereof, and a derivative thereof or polytetrafluoroethylene, polyhexafluoropropylene, polydifluoroethylene, polyvinyliden fluoride, polyvinyl fluoride, and a copolymer thereof. They may also consist partially or fully of the oxide, hydroxide, carbonate, sulfates, phosphate, metasilicate, borate, oxalate, tungstate, molybdate, vanadate, chromate, selenate, and manganate of a metal or the metal itself selected from the group consisting of: titanium, zirconium, silicon, zinc, iron, manganese, aluminum, magnesium, nickel, copper, silver, barium, calcium, scandium, bismuth, molybdenum, niobium, neodymium, antimony, selenium, stannum, strontium, terbium, tellurium, thorium, yttrium, and combinations thereof. MSM adsorbents may also be included as coatings, admixtures of the above or alone.

In one embodiment, the invention comprises a modified polyamine comprising: a hybrid inorganic/organic material comprising a polyamine and an inorganic material having one or more characteristics selected from the group consisting of: amorphous structures, high surface areas, large pore volumes, and nanocrystalline structures. In one embodiment, the inorganic material is an inorganic oxide material.

In one embodiment, the invention comprises a modified polyamine comprising a polyamine impregnated into or attached to a porous inorganic or organic microbead. In one embodiment, the polyamine is coupled to one or more microbeads.

In one embodiment, the invention comprises a modified polyamine which comprises a polyamine having inorganic molecules or organic molecules, or both, chemically attached to it.

In one embodiment, the invention comprises a modified polyamine which comprises a bio-compatible copolymer of a polyamine and a dermatologically compatible aqueous-soluble and/or oil-soluble polymer.

In one embodiment, the invention comprises a nanostructured polyamine which comprises a polyamine reacted with one or more crosslinkers.

In one embodiment, the polyamine is selected from the group consisting of one or more of the following: amine-containing polysaccharides, amine-containing polypeptides, polyethylenimine, polyethylenimine derivatives, poly(vinylamine), poly(diallylamine), poly(allylamine), copolymers of diallylamine and allylamine, copolymers containing diallylamine or allylamine, copolymers containing diallylamine and allylamine, and condensation polymers formed from polyamine monomers and monomers with two or more amine-reactive groups.

In another embodiment, the polyamine is selected from the group consisting of one or more of the following: poly(l-ysine), polyethylenimine, polyethylenimine derivatives, poly(vinylamine), polymers containing diallylamine, and polymers containing allylamine.

In one embodiment, the invention comprises an article comprising: a liquid pervious topsheet; a backsheet; and an absorbent core intermediate between said backsheet and said topsheet. In one embodiment, the absorbent core comprises from about 0.5 g/m² to about 500 g/m² of a cationic polysaccharide comprising an aminopolysaccharide selected from the group consisting of one or more of the following: chitosan, chitosan salt, crosslinked chitosan and a mixture thereof; and from about 0.1 g/m² to about 250 g/m² of an acidic pH buffering means having a pH in the range of from about 3.5 to about 6.5 and comprises a weak acid having its pKa or at least one of its pKas in the range from about 3.5 to about 6.5 and its conjugate base; and from about 5 g/m² to about 250 g/m² of absorbent gelling material.

In one embodiment, the cationic polysaccharide is selected from the group consisting of one or more of the following: chitosan, chitosan salt, crosslinked chitosan and a mixture thereof having a degree of deacetylation of more than about 75%.

In one embodiment, the chitosan salt is selected from the group consisting of one or more of the following: citric acid, formic acid, acetic acid, N-acetylglycine, acetylsalicylic acid, tlimaric acid, glycolic acid, iminodiacetic acid, itaconic acid, lactic acid, maleic acid, inalic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isoleucine, prolinephenylalanine, tryptophan, methionine, glycine, serine, cysteine, tyrosine, asparagine, glutamine, lysine, arginine, hydroxyproline, pyrrolidone carboxylic acid, chitosonium pyrrolidone carboxylate and mixtures thereof.

In one embodiment, the pH buffering means is selected from the group consisting of one or more of the following: citric acid/sodium hydroxide, citric acid/sodium citrate, citric acid/potassium citrate, oxalic acid/sodium oxalate, tartaric acid/potassium hydrogen tartarate, oxalic acid/potassium tetra oxalate dihydrate, phthalic acid/potassium phthalate, phthalic acid/sodium phthalate acetic acid/sodium acetate, benzoic acid/sodium benzoate, glutaric acid/sodium glutarate, adipic acid/sodium adipate, carbonic acid/sodium carbonate and mixture thereof and most preferably is citric acid/sodium citrate, citric acid/sodium hydroxide and/or citric acid/potassium citrate.

In one embodiment, the invention comprises an additional odor control agent selected from the group consisting of one or more of the following: zeolites, silicates, activated carbons, diatomaceous earth, cyclodextrine, clay, chelating agents, ion exchange resins, perfumes and mixture thereof. In one embodiment, the level of the additional odor control agent or a mixture thereof is from about 0.5 g/m² to about 600 g/m².

In one embodiment, the invention comprises a method of controlling odor associated with DMSO and related odorous metabolites wherein said bodily fluids are contacted with an odor control system comprising a cationic polysaccharide, selected from the group consisting of one or more of the following: chitosan, chitosan salt, crosslinked chitosan and a mixture thereof, and an acid pH buffering means typically having a pH in the range of about 3.5 to 6.5.

In one embodiment, the invention comprises an odor eliminating fiber structure having an indicator comprising a fiber substrate containing odor eliminating fibers, a surface thereof being visibly determined for change of odor eliminating power with a difference between a color of the fiber substrate discoloring through adsorption of a smelling gas and a color of a standard color display part.

In one embodiment, the color of the standard color display part provided on the surface of the fiber substrate becomes difficult to be distinguished by discoloration of the fiber substrate through adsorption of a smelling gas.

In one embodiment, the color difference between the color of the fiber substrate upon losing the odor eliminating power and the color of the standard color display part provided on the surface of the fiber substrate is 4 or more grades upon evaluation with gray scale for assessing change in color.

In one embodiment, the odor eliminating fibers contain at least one odor eliminating component selected from silver, copper and a metallic compound thereof, and a content of silver and/or copper is 0.1% by weight or more of the total fiber substrate.

In one embodiment, the odor eliminating fibers comprises an odor eliminating component-containing crosslinked acrylate fibers containing at least one odor eliminating component selected from silver, copper and a metallic compound thereof, and content of a silver and/or copper is 0.1% by weight or more of the total acrylate fibers.

In one embodiment, one surface of the fiber substrate has an easy-sticking and easy-releasing function.

The odor-absorbing fabric may be used in the manufacture of a disposable absorbent article selected from the group consisting of one or more of the following: a patient bedcover, patient gown, caregiver scrubs, gowns, masks, or any other required item to be worn or used to protect the patient or staff or visitors.

The patient bedding may comprise one or more of the following: suitably large sheets of odor absorbing material which may be coated partially or fully with slightly adhering material to prevent slippage. They may be assembled using methods well known in the art of clothing manufacture, including thermal, ultrasonic or electronic sealing, hot melt, adhesives, sewing, multineedle sewing, serging, basting, binding, or other joining methods. Seams may be folded, lapped, flat felled, straight stitched, frenched, overcast, enclosed, bound, hemmed, reinforced, top stitched, or other suitable seaming method. This bedding can be used at all times while the patient is undergoing treatment using DMSO and related compounds.

The clothing and mask items for the patient and for the caregivers may be shaped and formed to provide the maximum freedom of movement and access. These items may be constructed of cut sheets of odor absorbing material and may include ties, belts, snaps, or other fasteners to maintain the position of the article. These items may be assembled using thermal, ultrasonic or electronic sealing, hot melt, adhesives, sewing, multineedle sewing, serging, basting, binding, or other joining methods. Seams may be folded, lapped, flat felled, straight stitched, frenched, overcast, enclosed, bound, hemmed, reinforced, top stitched, or other suitable seaming method. These items can be used at all times while the patient is undergoing treatment using DMSO and related compounds. The clothing and mask items described herein may comprise any or all of the DMSO and related odorous metabolite capturing capabilities and features of embodiments described herein.

In one embodiment, the invention comprises a method of providing disposable, strong, absorbent DMSO and related odorous metabolite capturing health care bedding which comprises providing DMSO and related odorous metabolite capturing fabric plus a non-woven fabric comprised of randomly entangled mixtures of natural and synthetic fibers interconnected so that the individual fibers are held in place to form a coherent, stable, strong fabric having a high absorbency capacity; cutting the fabric to the desired length in the cross direction; and converting said fabric to a desired size and shape. Such material may also comprise any or all of the DMSO and related odorous metabolite capturing capabilities and features of embodiments described herein.

In one embodiment, the natural fiber is cellulosic wood pulp. In one embodiment, the synthetic fiber is selected from the group consisting of one or more of the following: a polyester, a nylon, a rayon, a polypropylene and mixtures thereof. In one embodiment, the synthetic fiber is polyester.

In one embodiment, the invention comprises a method of providing disposable strong, absorbent DMSO and related odorous metabolite capturing health care bedding which comprises employing as the bedding material DMSO and related odorous metabolite capturing fabric principally composed of polyester fibers combined with cellulosic wood pulp fibers, said fibers locked into place by a three-dimensional fiber entanglement wherein the individual fibers are intertwined, tangled and interconnected to each other so as to be virtually inseparable, said fabric having an absorptive capacity of at least that of woven fabric made of natural fibers, cutting the fabric to a desired length in the cross direction, and converting said cut fabric to a desired size and shape. Such material may also comprise any or all of the DMSO and related odorous metabolite capturing capabilities and features of embodiments described herein.

In one embodiment, the fabric has a weight of about 0.5 to about 10 ounces per square yard.

In one embodiment, after cutting said bedding material in the cross (CD) direction, a strip of elastic is attached along the edges to provide a close fit to a platform it is to cover. The platform may be a six-sided gurney.

In one embodiment, the invention comprises a method of providing disposable, strong, moisture absorbent DMSO and related odorous metabolite capturing health care bed and gurney coverings comprising: employing as the bedding material DMSO and related odorous metabolite capturing fabric principally composed of polyester fibers combined with cellulosic wood pulp fibers, said fibers interlocked by a three-dimensional fiber entanglement, wherein the individual fibers are intertwined, tangled and interconnected to each other so as to be virtually inseparable, and wherein said fabric has an absorptive capacity higher than that of conventional bedding made from cotton-polyester blends. In another embodiment, the method further comprises cutting across the fabric and converting said bedding material to a desired shape suitable for a gurney covering, so that its strongest direction is along the cut direction of the covering. Such material may also comprise any or all of the DMSO and related odorous metabolite capturing capabilities and features of embodiments described herein.

A breathable DMSO and related odorous metabolite capturing composite having hydrostatic head according to IST 80.4-92 of at least about 4 inches comprising a laminate of at least one fibrous, nonwoven web layer and at least one thermoplastic film layer, the laminate being stretched no more than about 5% in a lengthwise and widthwise direction, and wherein the film layer comprises at least one thermoplastic resin, a finely divided particulate material capable of promoting breathability, and a plurality of point-like deformations which provide breathability of the composite, wherein the breathable composite has a breathability of at least about 500 $g/m^2/day$. Such material may also comprise any or all of the DMSO and related odorous metabolite capturing capabilities and features of embodiments described herein.

In one embodiment, the composite has a MVTR of at least about 500 $g/m^2/day$, wherein the laminate can be stretched to less than about 5% lengthwise or widthwise stretching.

In one embodiment, the fibrous nonwoven web layer comprises filaments comprising at least one polyolefin resin.

In one embodiment, the thermoplastic film layer comprises at least one polyolefin resin.

In one embodiment, the thermoplastic film layer comprises at least one polyolefin resin and the nonwoven web layer comprises filaments comprising at least one polyolefin resin.

In one embodiment, the nonwoven web layer has substantial segments of filaments unadhered to the film layer whereby a cloth texture suitable for diaper and apparel uses is provided on at least one surface of the composite.

In one embodiment, the composite has a hydrostatic head of at least about 7 inches.

In one embodiment, the polyolefin resin of the thermoplastic film layer comprises at least one polyethylene resin. In one embodiment, the polyolefin resin of the thermoplastic, breathable film layer comprises at least one polypropylene resin.

In one embodiment, the polyolefin resin of the filaments comprises at least one polyethylene or polypropylene resin. In one embodiment, the polyolefin resin of the filaments comprises at least one polyethylene resin.

In one embodiment, the invention comprises a breathable composite DMSO and related odorous metabolite capturing material comprising a laminate comprising at least one film layer and at least one nonwoven web layer, the laminate being no more than insignificantly stretched in a lengthwise and widthwise direction, and wherein the nonwoven web layer comprises filaments of at least one polyolefin resin, and the film layer comprises a polyolefin resin, a finely divided particulate material capable of promoting breathability, and a plurality of embossed, point-like deformations, such deformations providing breathability of the composite by occupying about 8 to about 40% of the area of a surface of the composite and being present on such surface at a density of about 100 to 500 points per square inch. Such material may also comprise any or all of the DMSO and related odorous metabolite capturing capabilities and features of embodiments described herein.

In one embodiment, the polyolefin resin of the film layer comprises at least one polyethylene resin.

In one embodiment, the nonwoven web layer comprises a web of substantially continuous filaments.

In one embodiment, the filaments comprise at least one polypropylene resin. In one embodiment, the filaments of the web of substantially continuous filaments provide a cloth texture to said nonwoven web layer on at least one surface of the composite. In one embodiment, the filaments comprise at least one polyethylene resin. In one embodiment, the filaments of the web of substantially continuous filaments provide a cloth texture to said nonwoven web layer on at least one surface of the composite.

In one embodiment, the nonwoven web layer comprises a web of staple fibers.

In one embodiment, the staple fibers comprise at least one polypropylene resin. In one embodiment, the staple fibers of the web of staple fibers provide a cloth texture to said nonwoven web layer on at least one surface of the composite. In one embodiment, the staple fibers comprise at least one polyethylene resin. In one embodiment, the staple fibers of the web of staple fibers provide a cloth texture to said nonwoven web layer on at least one surface of the composite.

In one embodiment, the polyolefin resin of the film layer comprises at least one polypropylene resin.

In one embodiment, the nonwoven web layer comprises a web of substantially continuous filaments comprising at least one polypropylene resin. In one embodiment, the nonwoven web layer comprises staple fibers comprising at least one polypropylene resin. In one embodiment, the nonwoven web layer comprises a web of substantially continuous filaments comprising at least one polyethylene resin. In one embodiment, the nonwoven web layer comprises staple fibers comprising at least one polyethylene resin.

In another embodiment, the adsorbent materials/fibers described herein are incorporated into one or more portions of a disposable gown for DMSO treated medical patients, such as the gown described in U.S. Pat. No. 4,819,275, the entire contents of which are incorporated herein by reference. This patent describes a disposable, double-breasted gown for medical patients formed, without sewing, of non-woven synthetic plastic fabric sheeting which is soft and ultrasonically sealable, said gown comprising: a body formed from a rectangular blank having a straight upper long edge that is die cut to form chamfered corners on either side, an off-center arcuate neck indentation and isosceles triangular arm hole indentations on the left and right sides of the arcuate indentation, the resultant straight edge shoulder segments formed between the corners and the indentations all having the same length and a common line, the peaks of the triangular indentations being aligned with parallel left and right transverse fold lines that define between the lines a rear gown section on one side of which is a relatively narrow left-front section and on the other side of which is a broad right-front section, the left-front section being folded over the rear section and the right-front section being folded over the folded left-front section to overlap this section, the straight edge segments of the left and right front sections being ultrasonically seamed to the corresponding segments of the rear section to define left and right arm holes; and a pair of sleeves whose inlets are ultrasonically seamed to the arm holes of the body, each sleeve being formed of a relatively small rectangular blank having at its upper edge an isosceles triangular indentation whose peak is aligned with a center transverse fold line, and having a straight lower edge, such that when this blank is folded in half, and the folded over lower straight edge is ultrasonically seamed, this creates a tubular sleeve having an inlet which is ultrasonically seamed to the arm holes of the body of the gown.

In one embodiment, the adsorbent materials/fibers described herein are incorporated into one or more portions of a surgical gown or scrubs for caregivers of DMSO treated patients, such as the type described in U.S. Pat. No. 4,171,542, the entire contents of which are incorporated herein by reference.

The gown described in U.S. Pat. No. 4,171,542 has sleeves, a front portion having a chest area covering the chest of the user and side portions which close and overlap at the back of the user, a bib affixed about its periphery to the inside surface of the surgical gown at the chest area with a portion of the bib inwardly of the periphery remaining unsecured to the gown, the chest area having a pair of spaced, substantially vertical slits formed therein within the confines of the peripheral portions of the bib, the slits communicating with the unsecured portion of the bib and being of a length to allow passage of the user's hands therethrough whereby the bib provides a sterile hand support pocket maintaining the user's hands in the aseptic zone bounded by the user's neck, shoulders and waist line.

In another embodiment, the adsorbent materials/fibers described herein are incorporated into one or more portions of a disposable face mask for caregivers of DMSO treated patients. Exemplary masks include those described in U.S. Pat. Nos. 6,055,982; 5,765,556 and 5,322,061, herein incorporated by reference. In general, the masks described in these patents comprise a filter body having an opening sized to cover the nose and mouth of a wearer, the body having top and bottom edges with the top edge arranged to extend across the nose of the wearer and the bottom edge arranged to extend under the chin of the wearer; the top edge having ends opposite from each other and the bottom edge having ends opposite from each other; first securing means attached to the filter body adjacent to each end of the top edge and arranged to extend generally about the back of the head of the wearer in an approximate linear continuation from the top edge, the first securing means for urging the top edge into tight engagement with the wearer to prevent fluid flow between the top edge and the wearer; second securing means attached to the filter body adjacent to each end of the bottom edge and arranged to extend generally over the top of the head of the wearer in an approximate linear continuation from the bottom edge, the second securing means for urging the bottom edge into tight engagement with the wearer to prevent fluid flow between the bottom edge and the wearer; the filter body comprising an upper portion of generally trapezoidal configuration having a longer side forming the top edge and a lower portion of generally trapezoidal configuration having a longer side forming the bottom edge; the upper and lower portions being joined along all remaining sides; a plurality of radii formed on opposite sides of the filter body extending from the opening; a first strip of sealing material disposed within the filter body adjacent to the opening and extending along the top edge; a second strip of sealing material disposed within the filter body adjacent to the opening and extending along the bottom edge; and the first sealing strip and the second sealing strip cooperating with each other to form a fluid barrier between the opening of the filter body and the face of the wearer.

In one embodiment, color changes indicate adsorption. Color changes upon adsorbing odors may be tested as follows based on several methods, including but not limited to that described in US Patent Publication No. 20030190266, herein incorporated by reference:

|  | Color of fiber substrate Odor eliminating power (%) |  | Visibility of display part Odor eliminating power (%) |  |  |  |  | Color difference on saturated adsorption |
| --- | --- | --- | --- | --- | --- | --- | --- | --- |
|  | 100 | 0 | 100 | 75 | 50 | 30 | 0 | (grade) |
| Example 1 | light beige | light umber | 1 | 1 | 2 | 3 | 4 | — |
| Comparative Example 1 | — | white | no odor eliminating power |  |  |  |  | — |
| Example 2 | light beige | light umber | 4 | 3 | 3 | 2 | 1 | 4-5 |
| Example 3 | light dark green | brown | 4 | 3 | 2 | 2 | 1 | 4-5 |
| Example 4 | Beige | umber | 4 | 3 | 2 | 2-1 | 1 | 4-5 |
| Example 5 | very light beige | beige | 3 | 3 | 2 | 2 | 1 | 4-5 |

Mask

In one embodiment, the invention comprises a mask that is designed to reduce, eliminate or shield the user from odors associated with DMSO and related compounds. Embodiments described above that relate to the fabric may be used to construct some embodiments of the mask.

Figure 3:
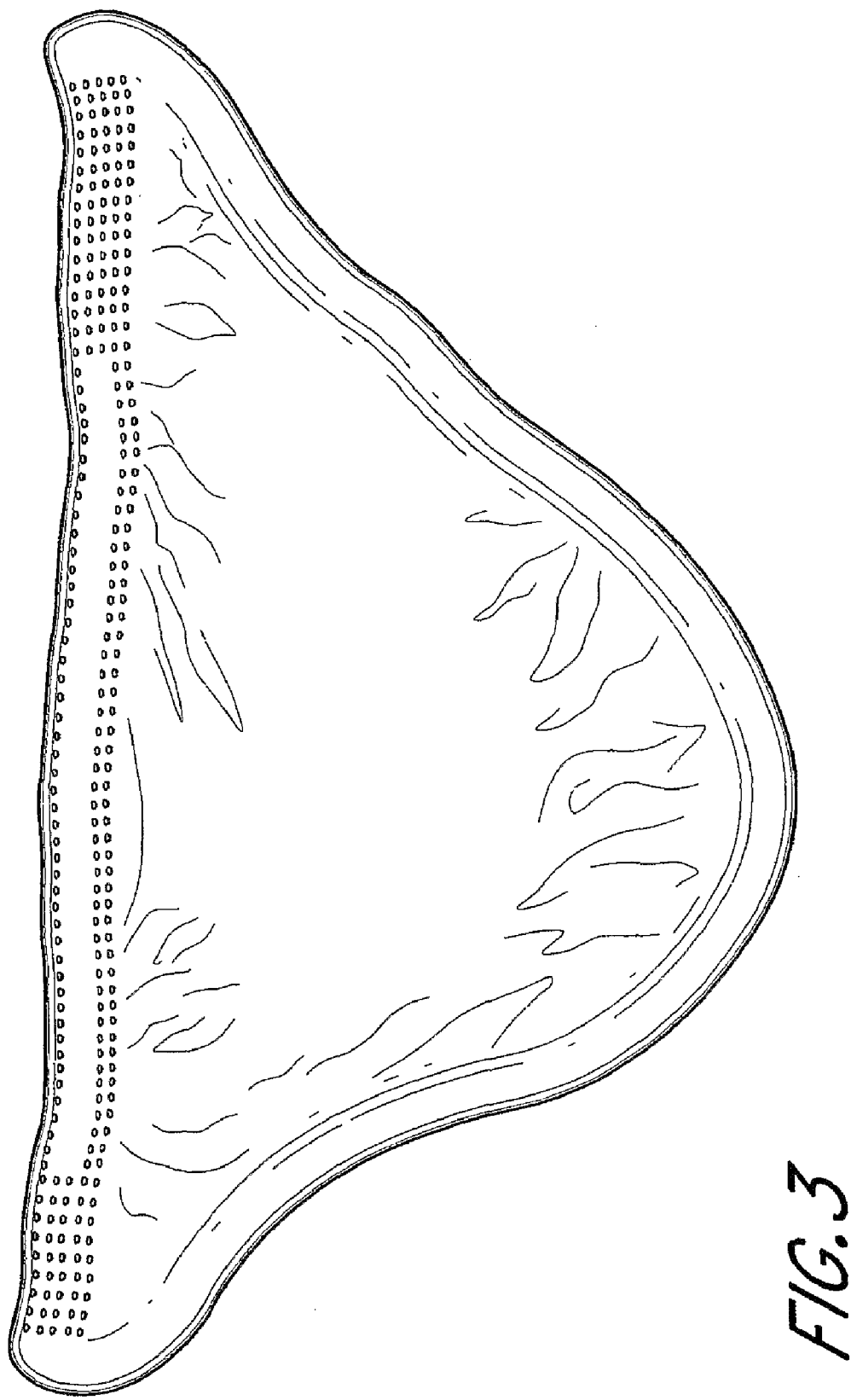
FIG. 3 shows a front view of a "duckbill" type odor-absorbing mask according to one embodiment.
Figure 4:
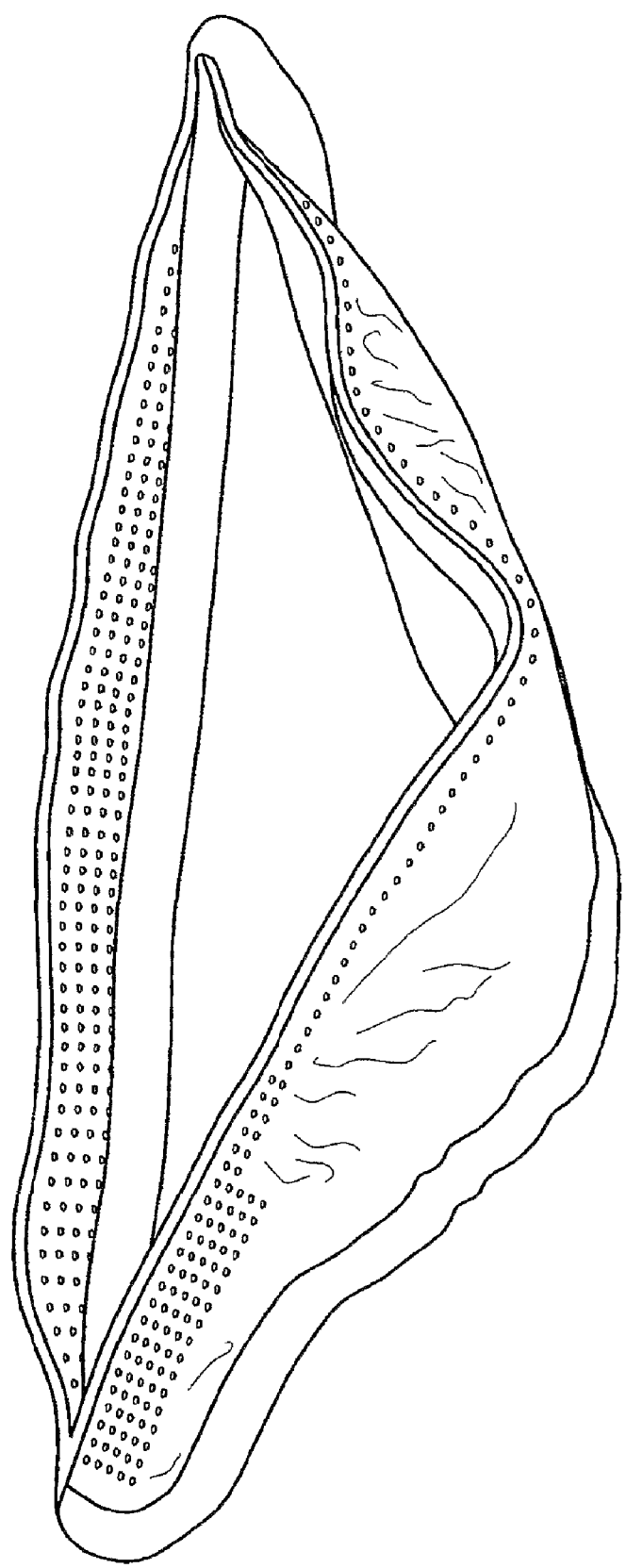
FIG. 4 shows a front view of a "duckbill" type mask according to one embodiment, showing the mask partially open.
Figure 5:
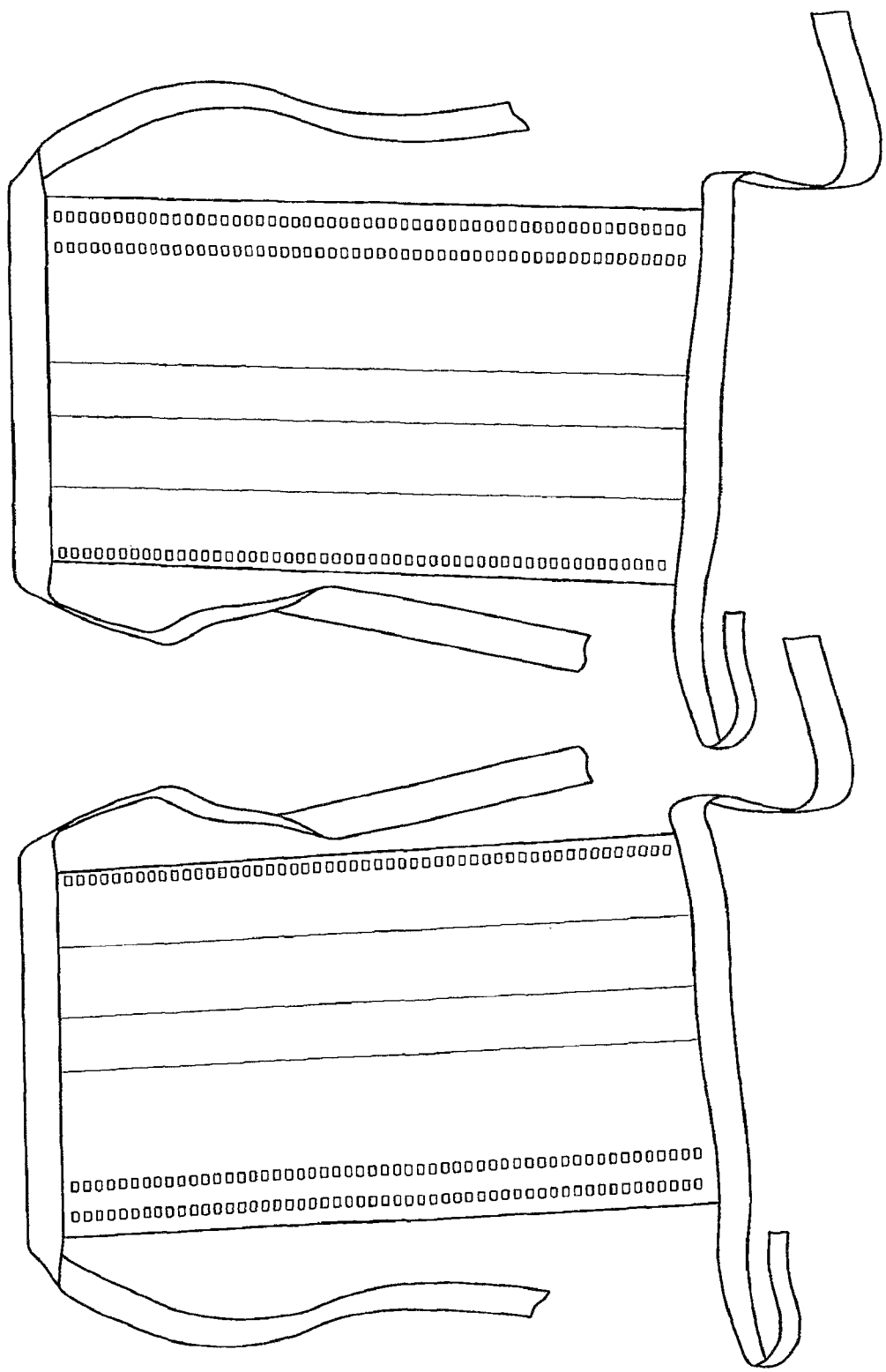
FIG. 5 shows a surgical mask according to one embodiment.

In one embodiment, the mask comprises one or more layers. The face mask may be a "duckbill" type mask (FIGS. 3-4), or surgical mask (FIG. 5). In one embodiment, an exhale valve comprising two flat strips of elastomer is installed in place of the entire seam at the bottom of the duckbill mask which has a large cross-sectional area when open. The surgical masks may also comprise one or more odor-masking "scratch and sniff" patches which release one or more pleasant odors when abraded. Such odors include lemon, perfume, peppermint, vanilla and the like. These patches may be square, circular rectangular or any other desired shape.

In one embodiment, the layers include from outer (distal to the face) to inner (proximal to the face): 1) outer shield; 2) copper layer; 3) carbon layer; 4) chemical layer; and 5) facial layer. In another embodiment, the mask comprises one or more of these layers. The layers need not be present in the order identified above.

The outer shield may provide N95 or N99 filtration. In one embodiment, the mask filters at least about 75%, 80%, 85%, 90%, 95%, 97%, 99%, 99.9%, or 100% of airborne particles. The outer shield layer may comprise 100% synthetic fiber. Examples of synthetic fibers include those described herein, and other synthetic fibers well known in the art (e.g., polyester, rayon, acrylic, nylon, dacron).

The copper layer may act as a catalytic converter. The copper layer may comprise one or more fibers and powdered copper. In one embodiment, the fiber comprises about 40% wood pulp and about 60% synthetic fiber. The powdered copper may be present on the fiber in an amount ranging from about 100% w/w to about 500% w/w, preferably from about 200% w/w to about 400% w/w, and more preferably about 250% w/w.

The carbon layer may comprise activated charcoal and acts as an odor adsorber. In one embodiment, the carbon layer comprises two sub-layers: activate charcoal adsorber I and activated charcoal adsorber II. The carbon layer may comprise one or more fibers and activated carbon. In one embodiment, the fiber comprises about 40% wood pulp and about 60% synthetic fiber. The activated carbon may be present on the fiber in an amount ranging from about 100% w/w to about 500% w/w, preferably from about 200% w/w to about 400% w/w, and more preferably about 250% w/w. One or more types of activated carbon may be incorporated into the carbon layer. In one embodiment, the following Chemsorb activated carbon compositions are used: 1202-70 G12 (for acid gases), 620-70 G12 (for ammonia and amines), 1505-70 G12 (for aldehydes) and 1000-70 (for organic vapors).

The chemical layer may allow breath-activated odor removal. The chemical layer comprises one or more fibers and one or more odor-removing chemicals, which may be breath-activated, such as citric acid, chitosan, MSM and other compounds. In one embodiment, the chitosan, citric acid and MSM may be present on the fiber in amounts of about 50% w/w, about 40% w/w and about 30% w/w, with the remainder being one or more other compounds.

The facial layer may provide soft facial protection. The facial layer may comprise 100% synthetic fiber. In one embodiment, natural fibers are used, alone or in combination with synthetic fibers.

In one embodiment, the mask is made by placing the coatings on separate layers prior to forming the masks on the same multi-sheet airlay machine.

Clean Air Supply Assembly

In one embodiment, the present invention comprises a system for removing odors and chemicals resulting from the treatment of patients with DMS0 and related compounds. In one embodiment, this system is a clean air supply assembly.

In one embodiment, the invention comprises a rollably positioned, adjustably directable clean air supply assembly and enclosure for use in DMSO treated medical patient environments. The clean air supply assembly provides, in some embodiments, localized clean air free of the odors, DMS (dimethyl sulfide) and compounds resulting from the metabolism of DMSO and DMSO associated compounds including, but not limited to, hydrogen sulfide and methyl mercaptan.

In one embodiment, the clean air supply assembly comprises a fully portable device providing for the effective capture and movement of room air through an adsorbent material suitable for the complete removal of the metabolites of DMSO and other related compounds. This device may have battery power for backup or for use while moving a patient. In one embodiment, the device is capable of turning any hospital room into a virtual clean room.

In another embodiment of the present invention, a portable curtaining containment system which may encompass the patient's upper torso or the entire patient bed area with provisions for caregiver access is provided.

In one embodiment, the invention comprises a rollably positioned, passable through doorways, adjustably directable clean air supply assembly which provides air free of the metabolites of DMSO and others for use in an area where a patient is being treated using DMSO and associated compounds. The clean air supply assembly may comprise one or more of a base module, a powered air moving assembly and a filtration system.

Figure 2:
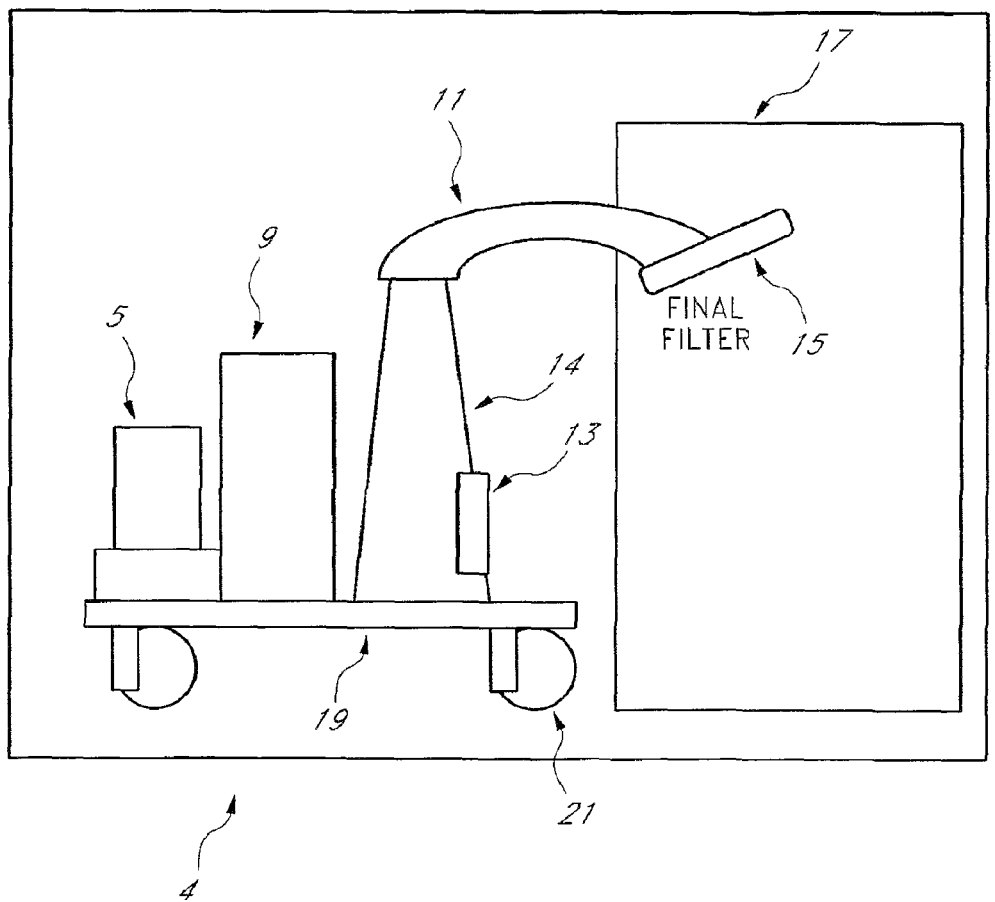
FIG. 2 is a schematic diagram of a rollably positioned, adjustably directable clean air delivery supply assembly and enclosure according to one embodiment.

The clean air supply assembly 4 is shown schematically in FIG. 2 and comprises a rollable support assembly 19 having wheels 21. Attached to the platform are a power supply unit 5 powering an electronics package 7 providing either DC or AC power depending on the motor selected. In one embodiment, the power supply unit 5 comprises a battery with a charger. An internal or external chemical and/or odor filter and adsorbent cartridge 9 containing an adsorbent is mounted on platform 19 adjacent power supply unit 5 and electronics package 7.

In one embodiment, the adsorbent cartridge 9 follows the air moving assembly and is capable of removing metabolites of DMSO and other related compounds, and may incorporate visual indication of depletion of such metabolites. The adsorbent may be augmented or replaced by ultraviolet lamps and/or ozone (e.g., ozone injection) to further or fully remove odors, DMS, methyl mercaptan and/or hydrogen sulfide and other chemicals.

In one embodiment, clean air supply assembly 4 directs a controlled amount of clean grade air through an adjustably oriented top hood assembly 11 which contains a pre-filter 13 and a sealed final filter 15 (e.g., high efficiency particle arrestor (HEPA) filter) which may be mounted within the lower portion of the base 14 or within the top final filter hood assembly 11. This final filter 15 filters the air and allows the discharge of the air at minimal-eddy creating air velocities for improved air quality levels, which creates certifiable cleanrooms, clean zones, improved recirculated air quality within an given area, where a patient is being treated with DMSO. The clean air supply assembly 4 is shown optionally attached to a patient isolation unit 17.

In one embodiment, the clean air supply assembly is a modification of the clean air supply assembly shown in FIG. 2 of U.S. Pat. No. 6,099,607, the entire contents of which are incorporated herein by reference. In this device, the rollable support assembly in U.S. Pat. No. 6,099,607 is extended in a direction opposite the hood top assembly 328, and the battery/power module/adsorbent cartridge assembly shown in FIG. 2 of the present application is placed on, or attached to, the rollable support assembly. This device may be attached to a wheelchair or gurney via a wheelchair/gurney attachment, and filters odors and chemicals resulting from DMSO treatment of a patient.

The clean air supply assembly according to one embodiment of the present invention may also be attached to a patient isolation unit comprising a frame body foldable and/or capable of being disassembled; and a flexible envelope adapted to be detachably attached to the frame body as assembled as described in U.S. Pat. No. 6,099,607. The patient isolation unit may also comprise a collapsible framework constructed of rods pivotally joined at their ends to hubs to form a self-standing unit when expanded and to fold into a small set of nearly parallel rods when folded as described in U.S. Pat. Nos. 4,986,016 and 5,125,205, the entire contents of which are incorporated herein by reference.

In another embodiment, the exhauster device 5 shown in FIG. 1 of U.S. Pat. No. 6,966,937, herein incorporated by reference, is modified by extending the rollable support assembly in a direction opposite exhaust duct 4 and the battery/power module/adsorbent cartridge assembly shown in FIG. 2 of the present application is placed on, or attached to, the rollable support assembly. The device may then be attached to a patient isolation unit to filter odors and chemicals resulting from DMSO treatment of a patient.

The patient isolation unit may include an integral patient isolation curtain rod, or a separate foldable frame body, and a flexible envelope made of a natural or polymeric porous or nonporous film, knit, woven or non-woven sheet which can be attached to the assembled frame body, which may or may not include a bottom.

In one embodiment, the patient isolation assembly includes a low cost disposable curtain to be affixed to the patient privacy curtain, or to an inexpensive plastic frame.

Indicator

The present invention also provides a visual color indicator, particularly a metal permanganate visual color indicator material suitable for the detection of DMS and other metabolites of DMSO. In one embodiment, sulfides such as DMS are oxidized by potassium permanganate to produce sulfone with the resulting reduction of the permanganate ion eliminating its characteristically intense purple color. The indicator may be included in any one of the layers of the adsorbant described herein, or in an additional layer on a base layer having one, two, or three parts. In one embodiment, an indicator for DMS and the metabolites of DMSO and other related compounds includes core particles containing an adsorbing material as described herein in which the intermediate layer comprises one or more indicators and a metal or other compound, and is disposed between the core particles and the porous coating layer. The structure and components of the core particles are described in detail above. Visual indicators other than color may also be used. One or more indicators may be included within a layer, on the inner surface of a layer, on an outer surface of a layer, or integral with one of the layers.

In another embodiment, the present invention comprises a system which includes a transparent container with a packed bed containing the detecting indicator of the present invention. In one embodiment, the packed bed functions as a holder for the indicator material and may be separate from, or included in, an indicating adsorbent bed utilized for the removal of DMS and other DMSO metabolites. In one embodiment, as the indicator is exposed to DMS, methyl mercaptan and related materials, it becomes progressively lighter and the lightening progresses through the bed.

In a further embodiment, the present invention includes a personal monitor comprising one or more detecting indicators to sample airborne contaminants by the process of diffusion. Exposure levels may then be compared to permissible exposure limits published in health and safety standards. In one embodiment, the lighter the personal monitoring patch, the greater exposure is indicated.

In yet another embodiment, the present invention includes a standard format ambient air sampling tube for a standard air sampling pump such tube containing the detecting indicator. In one embodiment, the longer the lightened area, the more DMS, methyl mercaptan or other sulfide detected.

In one embodiment, the invention comprises a functional ambiance odor or sulfur chemical or DMS indicating and/or regulating member comprising the ambiance odor or sulfur chemical regulating member.

In one embodiment, the invention comprises an ambiance odor or sulfur chemical or DMS indicating and/or regulating member, comprising core particles containing at least one odor or sulfur chemical regulating material of an acid salt, and a porous coating layer including a polymer material that coats said core particles, wherein the acid salt is at least one of an alkali metal salt, an alkaline earth metal salt, and an ammonium salt.

In one embodiment, the odor or sulfur chemical regulating material is selected from the group consisting of one or more of the following: sodium sulfate, an alkali metal salt of phosphoric acid, an alkali metal salt of hydrogen phosphate, an ammonium salt of phosphoric acid, and an ammonium salt of hydrogen phosphate.

In one embodiment, the core particles further contains a hydrophilic polymer compound. In one embodiment, the hydrophilic polymer compound is selected from the group consisting of one or more of the following: vinyl alcohol, vinylpyrrolidone, acrylic acid, methacrylic acid, a saponification compound of vinyl acetate, a cellulose ester, an oxyolefin, and a sugar.

In one embodiment, the invention comprises any or all of the above indicting absorbents incorporated into a personal monitor sampling, detecting, and indicating airborne DMS and other odorous compounds resulting from the metabolism of DMSO and associated compounds by the process of diffusion.

In one embodiment, the invention comprises any or all of the above indicting absorbents incorporated into a standard format ambient air sampling tube for a standard air sampling pump such tube containing the detecting indicator for indicating airborne DMS and other odorous compounds resulting from the metabolism of DMSO and associated compounds.

EXAMPLES

The following examples describe non-limiting uses of the compositions, methods and apparatus described herein.

In one embodiment, a device to remove the odors and compounds resulting from the metabolism of DMSO and associated compounds directly from the patient's exhaled respiratory air is provided. In a preferred embodiment, the device (e.g., the adsorbent) is directly connected to the patient's mask. In one embodiment, this may require treating the highest concentration of odor bearing material.

In one embodiment, an apparatus to remove the odors and compounds resulting from the metabolism of DMSO and associated compounds from the exhaust outlet of a medical respiratory ventilator is provided. In another embodiment, the device is connected to the ventilator's exhaust outlet through a gas scavenging device. In one embodiment, the apparatus comprises a gas scavenging device comprising the adsorbent described herein, wherein the gas scavenging device is connected to the exhaust outlet. Thus, the DMSO metabolite-containing exhaust leaving the ventilator passes through the adsorbent which filters out the metabolites and odors, resulting in air that does not contain the odors associated with the metabolites.

In one embodiment, a device to remove the odors and compounds resulting from the metabolism of DMSO and associated compounds from the recirculated or vented stream a room sized HVAC or clean room system is provided. In one embodiment, the device (e.g., the adsorbent) is connected to the system's ductwork.

In one embodiment, an adsorbent to be adhered to or sandwiched between three dimensional fiber material as in fabric, cloth, felt, nonwoven or other flexible material to become part of clothing, bedding, masks and other items used by the patient or the medical staff is provided.

An article of patient bed covering to capture the odors and compounds emanating from the dermal areas of the patient and resulting from the metabolism of DMSO (dimethyl sulfoxide) and associated compounds is provided.

An article of patient clothing to capture the odors and compounds emanating from the dermal areas of the patient's body and resulting from the metabolism of DMSO (dimethyl sulfoxide) and associated compounds is also provided.

An article of caregiver clothing to capture the odors and compounds emanating from all areas of the patient including respiration and resulting from the metabolism of DMSO (dimethyl sulfoxide) and associated compounds is provided.

A caregiver mask to reduce and/or prevent the breathing by the caregiver of the odors and compounds emanating all areas of the patient including respiration and resulting from the metabolism of DMSO (dimethyl sulfoxide) and associated compounds is provided.

A device to remove the odors, DMS, methyl mercaptan and/or hydrogen sulfide and compounds resulting from the metabolism of DMSO and associated compounds directly from the area around a patient (e.g., the patient's upper torso) is provided. The flexible patient isolation assembly may or may not be connected to the clean air delivery assembly's top final filter hood assembly.

A device to remove the odors and compounds resulting from the metabolism of DMSO and associated compounds from the entire patient bed area with or without enough space for caregiver occupancy of the patient isolation assembly is provided. The clean air delivery assembly device may be connected to the patient isolation assembly sized to enclose only the bed or to provide caregiver access.

A device to remove the odors and compounds resulting from the metabolism of DMSO and associated compounds from the entire patient room is provided. The clean air delivery assembly may positioned with the top final filter hood assembly over the patient or preferably within the room should the patient be served by another unit.

A device to remove the odors and compounds resulting from the metabolism of DMSO and associated compounds directly from the area around the patient's wheelchair or gurney is provided. The portable clean air delivery assembly device may be connected to the wheelchair or gurney by means of clamps, straps or other suitable means. The flexible patient isolation assembly may or may not be connected to the clean air delivery assembly's top final filter hood assembly.

A device to indicate the presence of DMS and other odorous compounds resulting from the metabolism of DMSO and associated compounds directly from the patient's exhaled respiratory air is provided. Such compounds may be detected in concentrations of about 1 to about 10,000 parts per million. The device may be directly connected to the patient's mask.

A device to indicate the presence of DMS and other odorous compounds resulting from the metabolism of DMSO and associated compounds from the exhaust of a medical respiratory ventilator is provided. Such compounds may be detected in concentrations of about 1 to about 1,000 parts per million. The device may be integral to or connected to an adsorber located on the ventilator's discharge or directly on the ventilator's discharge through a gas scavenging device.

A device to indicate the presence of DMS and other odorous compounds resulting from the metabolism of DMSO and associated compounds from the recirculated or vented stream from a room sized HVAC or clean room system is provided.

Such compounds may be detected in concentrations of about 1 to about 10 parts per million. The device may be connected to the system's ductwork.

An indicating adsorbent included in a personal monitor containing the detecting indicator and sampling airborne contaminants by the process of diffusion is provided. Such compounds may be detected in concentrations of about 1 to about 1,000 parts per million. In some embodiments, such personal monitor may be pinned, clipped, or otherwise affixed to the clothing or person of the staff, visitors or patients in the medical facility.

An indicating adsorbent included in a standard format ambient air sampling tube for a standard air sampling pump such tube containing the detecting indicator is provided. Such compounds may be detected in concentrations of about 1 to about 10,000 parts per million. Such sampling may be from the patient's bed area, the room, the respiratory ventilator, the room's HVAC system, or other location.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for reducing the undesired odor associated with one or more metabolites of dimethyl sulfoxide (DMSO), comprising:
    transporting, via a medical ventilator, DMSO metabolite-containing air comprising one or more DMSO metabolites through said medical ventilator in use by a subject that has been treated with DMSO,
    wherein said medical ventilator comprises a first filter comprising a chemical odor removal layer and a HEPA filter,
    wherein the ventilator is configured to receive said DMSO metabolite-containing air,
    wherein the first filter comprises an adsorbent configured to adsorb said one or more DMSO metabolites from said DMSO metabolite-containing air,
    wherein said adsorbent comprises activated carbon, and
    capturing an amount of said one or more DMSO metabolites sufficient to reduce the associated odor by contacting said DMSO metabolite-containing air with said first filter, thereby decreasing the concentration of said one or more DMSO metabolites passing through said ventilator.

2. The method of claim 1, wherein said DMSO metabolite-containing air comprises one or more of methylsulfonylmethane (MSM) or dimethyl sulfide (DMS or methylthiomethane).

3. The method of claim 1, wherein said chemical odor removal layer comprises one or more of citric acid, chitosan, and MSM.

4. The method of claim 3, wherein said chemical odor removal layer comprises MSM and said DMSO metabolite-containing air comprises MSM.

5. A method for reducing the undesired odor associated with one or more metabolites of DMSO, comprising:
    transporting, via a medical ventilator, DMSO metabolite-containing air comprising one or more DMSO metabolites through said medical ventilator in use by a subject that has been treated with DMSO,
    wherein said medical ventilator comprises a first filter and a HEPA filter,
    wherein said first filter further comprises an indicator compound,
    wherein the ventilator is configured to receive said DMSO metabolite-containing air,
    wherein the first filter comprises an adsorbent configured to adsorb said one or more DMSO metabolites from said DMSO metabolite-containing air,
    wherein said adsorbent comprises activated carbon, and
    capturing an amount of said one or more DMSO metabolites sufficient to reduce the associated odor by contacting said DMSO metabolite-containing air with said first filter, thereby decreasing the concentration of said one or more DMSO metabolites assin throu h said ventilator.

6. The method of claim 1 or claim 5, wherein said HEPA filter further comprises an indicator compound.

7. The method of claim 1 or claim 5, further comprising passing said DMSO metabolite-containing air through an additional odor control agent selected from the group consisting of one or more of the following: zeolites, silicates, activated carbons, diatomaceous earth, cyclodextrine, clay, chelating agents, ion exchange resins, perfumes and mixture thereof.

8. A method for providing air having a reduced undesired odor associated with one or more metabolites of dimethyl sulfoxide (DMSO) comprising:
    conveying air comprising one or more DMSO metabolites having an undesired odor through a clean air member comprising:
    an adsorbent configured to adsorb said one or more DMSO metabolites or the odor associated therewith;
    a pre-filter;
    and a HEPA filter, and
    trapping an amount of said one or more DMSO metabolites or the odor associated therewith sufficient to reduce the associated odor by contacting said DMSO metabolites with said adsorbent, said pre-filter, and said HEPA filter to thereby provide air having a reduced undesired odor associated with one or more metabolites of DMSO.

9. The method of claim 8, wherein said one or more metabolites of DMSO are from an individual being treated with DMSO.

10. The method of claim 8, wherein said one or more metabolites of DMSO are from the environmental degradation of DMSO.

11. The method of claim 8, wherein said member is connected to the ductwork of a HVAC system.

12. A method for reducing undesired odors associated with one or more metabolites of dimethyl sulfoxide (DMSO) in the vicinity of a patient that has been treated with DMSO comprising:
    positioning said patient within a patient isolation unit coupled to a clean air supply assembly, said clean air supply assembly comprising:
    a first adsorbent configured to adsorb said one or more DMSO metabolites or the odor associated therewith;
    a pre-filter; and
    a HEPA filter, and
    said patient isolation unit comprising an odor-absorbing fabric article comprising a second adsorbent configured to adsorb said one or more DMSO metabolites or the odor associated therewith,
    conveying DMSO metabolite-containing air from said patient through said patient isolation unit;
    reducing the concentration of said one or more DMSO metabolites sufficient to reduce the associated odor by contacting said DMSO metabolite-containing air with said first adsorbent, said pre-filter, and said HEPA filter, thereby providing air having reduced undesired odors associated with said one or more metabolites of DMSO; and positioning said odor-absorbing fabric article comprising said second adsorbent around said patient, wherein said odor-absorbing fabric article comprising said adsorbent further reduces said one or more DMSO metabolites or the odor associated therewith.

13. The method of claim 12, wherein said first adsorbent comprises activated charcoal particles and said second adsorbent is selected from the group consisting of one or more of the following: chitosan, chitosan salt, crosslinked chitosan and a mixture thereof.

14. The method of claim 12, further comprising positioning said patient on bedding comprising an adsorbent configured to adsorb said one or more DMSO metabolites or the odor associated therewith.

15. The method of claim 14, wherein said bedding comprises a liquid pervious topsheet; a backsheet; and an absorbent core intermediate between said backsheet and said topsheet.

16. The method of claim 15, wherein said absorbent core comprises a cationic polysaccharide comprising an aminopolysaccharide selected from the group consisting of one or more of the following: chitosan, chitosan salt, crosslinked chitosan and a mixture thereof;

an acidic pH buffering means having a pH in the range of from about 3.5 to about 6.5; and an absorbent gelling material.

17. The method of claim 12, wherein said odor-absorbing fabric article is dimensioned to encompass the patient's upper torso or the entire patient bed area while still allowing caregiver access to the patient's upper torso.

18. The method of claim 17, wherein said odor-absorbing fabric article comprises polyester fibers optionally intertwined with cellulosic wood pulp fibers.

* * * * *